(12) United States Patent
Coulter

(10) Patent No.: US 8,911,777 B2
(45) Date of Patent: Dec. 16, 2014

(54) PHARMACEUTICAL COMPOSITION OF TACROLIMUS

(75) Inventor: Ivan Coulter, Dublin (IE)

(73) Assignee: Sigmoid Pharma Limited, Dublin (IE)

( * ) Notice: Subject to any disclaimer, the term of this patent is extended or adjusted under 35 U.S.C. 154(b) by 490 days.

(21) Appl. No.: 12/594,553

(22) PCT Filed: Apr. 4, 2008

(86) PCT No.: PCT/IE2008/000039
§ 371 (c)(1),
(2), (4) Date: Jul. 9, 2010

(87) PCT Pub. No.: WO2008/122966
PCT Pub. Date: Oct. 16, 2008

(65) Prior Publication Data
US 2010/0297221 A1 Nov. 25, 2010

Related U.S. Application Data

(60) Provisional application No. 60/907,490, filed on Apr. 4, 2007, provisional application No. 61/006,498, filed on Jan. 16, 2008.

(51) Int. Cl.
| | |
|---|---|
| *A61K 9/66* | (2006.01) |
| *A61K 36/00* | (2006.01) |
| *A61K 31/535* | (2006.01) |
| *A61K 31/44* | (2006.01) |
| *C12N 15/11* | (2006.01) |
| *A61K 9/00* | (2006.01) |
| *A61K 9/50* | (2006.01) |
| *A61K 31/436* | (2006.01) |
| *A61K 38/13* | (2006.01) |
| *A61K 45/06* | (2006.01) |

(52) U.S. Cl.
CPC ............ *A61K 9/0053* (2013.01); *A61K 9/5015* (2013.01); *A61K 9/5057* (2013.01); *A61K 9/5073* (2013.01); *A61K 31/436* (2013.01); *A61K 9/5026* (2013.01); *A61K 9/5047* (2013.01); *A61K 38/13* (2013.01); *A61K 9/50* (2013.01); *A61K 45/06* (2013.01)
USPC ........ 424/455; 424/725; 514/233.5; 514/291; 514/44 A

(58) Field of Classification Search
CPC . A61K 9/5015; A61K 9/5057; A61K 9/5073; A61K 45/06; A61K 31/436; A61K 9/5047; A61K 38/13; A61K 9/0053; A61K 9/50; A61K 9/5026
USPC .............. 424/455, 725; 514/233.5, 291, 44 A
See application file for complete search history.

(56) References Cited

U.S. PATENT DOCUMENTS

| | | |
|---|---|---|
| 4,279,632 A | 7/1981 | Frosch et al. |
| 4,379,454 A | 4/1983 | Campbell et al. |

(Continued)

FOREIGN PATENT DOCUMENTS

| | | |
|---|---|---|
| AU | 1977031116 | 12/1976 |
| AU | 627220 B2 | 8/1992 |

(Continued)

OTHER PUBLICATIONS

Cannon, "Oral Solid Dosage Forms of Lipid-based Drug Delivery Systems," *AM Pharm Rev* 8(1):108-115, 2005.

(Continued)

*Primary Examiner* — Blessing M Fubara
(74) *Attorney, Agent, or Firm* — Klarquist Sparkman LLP.

(57) ABSTRACT

An oral tacrolimus composition comprises minicapsules having a core containing tacrolimus in a solubilized liquid form. The minicapsules have a release profile to release the pre-solubilized tacrolimus throughout the entire gastrointestinal tract. The composition may be used, for example, for treatment or prevention of solid organ transplant rejection.

28 Claims, 4 Drawing Sheets

(56) References Cited

U.S. PATENT DOCUMENTS

| | | |
|---|---|---|
| 4,388,307 A | 6/1983 | Cavannak |
| 4,422,985 A | 12/1983 | Morishita et al. |
| 4,460,563 A | 7/1984 | Calanchi |
| 4,481,157 A | 11/1984 | Morishita et al. |
| 4,597,959 A | 7/1986 | Barr |
| 4,601,894 A | 7/1986 | Hanna et al. |
| 4,652,441 A | 3/1987 | Okada et al. |
| 4,656,161 A | 4/1987 | Herr |
| 4,695,466 A | 9/1987 | Morishita et al. |
| 4,748,023 A | 5/1988 | Tamás et al. |
| 4,749,574 A | 6/1988 | Ueda et al. |
| 4,751,241 A | 6/1988 | Motoyama et al. |
| 4,857,335 A | 8/1989 | Bohm |
| 5,102,668 A | 4/1992 | Eichel et al. |
| 5,145,684 A | 9/1992 | Liversidge et al. |
| 5,330,835 A | 7/1994 | Kikuchi et al. |
| 5,342,625 A | 8/1994 | Hauer et al. |
| 5,362,564 A | 11/1994 | Suzuki et al. |
| 5,385,737 A | 1/1995 | Shigeno et al. |
| 5,411,952 A | 5/1995 | Kaswan |
| 5,418,010 A | 5/1995 | Janda et al. |
| 5,478,508 A | 12/1995 | Suzuki et al. |
| 5,480,655 A | 1/1996 | Jizomoto et al. |
| 5,492,701 A | 2/1996 | Cervos et al. |
| 5,500,224 A | 3/1996 | Vranckx et al. |
| 5,510,118 A | 4/1996 | Bosch et al. |
| 5,529,783 A | 6/1996 | Burke et al. |
| 5,571,533 A | 11/1996 | Santus et al. |
| 5,645,856 A | 7/1997 | Lacy et al. |
| 5,650,232 A | 7/1997 | Glenn et al. |
| 5,665,386 A | 9/1997 | Benet et al. |
| 5,795,590 A | 8/1998 | Kiefer et al. |
| 5,827,531 A | 10/1998 | Morrison et al. |
| 5,843,347 A | 12/1998 | Nguyen et al. |
| 5,851,275 A | 12/1998 | Amidon et al. |
| 5,871,774 A | 2/1999 | Lemelson |
| 5,882,680 A | 3/1999 | Suzuki et al. |
| 6,022,562 A | 2/2000 | Autant et al. |
| 6,113,936 A | 9/2000 | Takebayashi et al. |
| 6,146,663 A | 11/2000 | Bissery et al. |
| 6,174,466 B1 | 1/2001 | Kiefer et al. |
| 6,190,692 B1 | 2/2001 | Busetti et al. |
| 6,251,661 B1 | 6/2001 | Urabe et al. |
| 6,267,985 B1 | 7/2001 | Chen et al. |
| 6,284,271 B1 | 9/2001 | Lundberg et al. |
| 6,309,663 B1 | 10/2001 | Patel et al. |
| 6,361,298 B1 | 3/2002 | Kiefer et al. |
| 6,429,089 B1 | 8/2002 | Matsuki |
| 6,457,339 B2 | 10/2002 | Komura |
| 6,531,150 B1 | 3/2003 | Sunohara et al. |
| 6,569,463 B2 | 5/2003 | Patel et al. |
| 6,585,997 B2 | 7/2003 | Moro et al. |
| 6,761,903 B2 | 7/2004 | Chen et al. |
| 6,923,988 B2 | 8/2005 | Patel et al. |
| 6,972,132 B1 | 12/2005 | Kudo et al. |
| 7,267,813 B2 | 9/2007 | Watanabe et al. |
| 7,374,779 B2 | 5/2008 | Chen et al. |
| 2001/0003589 A1 | 6/2001 | Neuer et al. |
| 2001/0024658 A1 | 9/2001 | Chen et al. |
| 2002/0009457 A1 | 1/2002 | Bowersock et al. |
| 2002/0098242 A1 | 7/2002 | Darder |
| 2003/0045516 A1 | 3/2003 | Luly et al. |
| 2003/0078194 A1 | 4/2003 | Cho et al. |
| 2003/0104048 A1 | 6/2003 | Patel et al. |
| 2003/0124061 A1 | 7/2003 | Roberts |
| 2003/0180352 A1 | 9/2003 | Patel et al. |
| 2003/0193102 A1 | 10/2003 | Yan |
| 2003/0232076 A1 | 12/2003 | Makino et al. |
| 2003/0235595 A1 | 12/2003 | Chen et al. |
| 2004/0028619 A1 | 2/2004 | Watanabe et al. |
| 2004/0029855 A1 | 2/2004 | Klaveness et al. |
| 2004/0062802 A1 | 4/2004 | Hermelin |
| 2004/0126428 A1 | 7/2004 | Hughes et al. |
| 2004/0230183 A1 | 11/2004 | Breegi et al. |
| 2005/0037077 A1 | 2/2005 | Legrand et al. |
| 2005/0095288 A1 | 5/2005 | Honea |
| 2005/0249807 A1 | 11/2005 | Brown et al. |
| 2006/0018965 A1 | 1/2006 | Moodley et al. |
| 2006/0034937 A1 | 2/2006 | Patel |
| 2006/0135441 A1 | 6/2006 | Khodadoust et al. |
| 2006/0222701 A1 | 10/2006 | Kulkarni et al. |
| 2007/0154554 A1* | 7/2007 | Burgermeister et al. ..... 424/486 |
| 2007/0274932 A1* | 11/2007 | Suginaka et al. ............... 424/59 |
| 2007/0292523 A1 | 12/2007 | Moodley et al. |
| 2007/0292932 A1* | 12/2007 | Panchaud-Mirabel ........ 435/176 |
| 2007/0299121 A1* | 12/2007 | Huhtinen et al. ............. 514/396 |
| 2008/0020018 A1 | 1/2008 | Moodley et al. |
| 2008/0107694 A1 | 5/2008 | Trogden et al. |
| 2008/0113031 A1 | 5/2008 | Moodley et al. |
| 2008/0311201 A1 | 12/2008 | Der-Yang et al. |
| 2008/0318912 A1 | 12/2008 | Fox et al. |
| 2010/0136105 A1 | 6/2010 | Chen et al. |
| 2010/0203120 A1 | 8/2010 | Coulter |
| 2010/0215737 A1 | 8/2010 | Coulter |
| 2010/0239665 A1 | 9/2010 | Coulter |
| 2010/0255087 A1 | 10/2010 | Coulter |

FOREIGN PATENT DOCUMENTS

| | | |
|---|---|---|
| CA | 2170748 | 8/1994 |
| CA | 2376261 | 6/2000 |
| CN | 1557283 | 12/2004 |
| DE | 19848849 | 10/1998 |
| EP | 0396425 | 11/1990 |
| EP | 0525731 | 2/1993 |
| EP | 0 550 067 | 7/1993 |
| EP | 0621775 | 11/1994 |
| EP | 0650721 | 5/1995 |
| EP | 0760237 | 3/1997 |
| EP | 0778083 | 6/1997 |
| EP | 0922451 | 6/1999 |
| EP | 0813876 | 3/2002 |
| EP | 0789561 | 4/2004 |
| EP | 1811979 | 11/2008 |
| JP | A-58 013508 | 1/1983 |
| JP | A-58 077810 | 5/1983 |
| JP | 59-088420 | 5/1984 |
| JP | A-61 151119 | 7/1986 |
| JP | 64-000015 | 1/1989 |
| JP | H0549899 A | 3/1993 |
| JP | 7247215 A | 9/1995 |
| JP | 2000-247911 | 9/2000 |
| JP | 2000-302654 | 10/2000 |
| JP | 64 000015 | 8/2010 |
| WO | WO 93/00063 | 1/1993 |
| WO | WO 97/02017 | 1/1997 |
| WO | WO 98/18610 | 5/1998 |
| WO | WO 98/50018 | 11/1998 |
| WO | WO 98/50033 | 11/1998 |
| WO | WO 99/06024 | 2/1999 |
| WO | WO 99/13914 | 3/1999 |
| WO | WO 00/00179 | 1/2000 |
| WO | WO 00/33862 | 6/2000 |
| WO | WO 00/69420 | 11/2000 |
| WO | WO 01/08666 | 2/2001 |
| WO | WO 01/37808 | 5/2001 |
| WO | WO 01/51008 | 7/2001 |
| WO | WO 01/80831 | 11/2001 |
| WO | WO 03/018134 | 3/2003 |
| WO | WO 03/020243 | 3/2003 |
| WO | WO 03/056938 | 7/2003 |
| WO | WO 03/092741 | 11/2003 |
| WO | WO 2004/022220 | 3/2004 |
| WO | WO 2004/042024 | 5/2004 |
| WO | WO 2004/064997 | 8/2004 |
| WO | WO 2004/084870 | 10/2004 |
| WO | WO 2005/020993 * | 3/2005 |
| WO | WO 2005/020994 | 3/2005 |
| WO | WO 2005/030205 | 4/2005 |
| WO | WO 2005/072088 | 8/2005 |
| WO | WO 2005/074913 | 8/2005 |
| WO | WO 2005/100454 | 10/2005 |
| WO | WO 2005/107721 | 11/2005 |
| WO | WO 2006/026592 | 3/2006 |

(56) References Cited

FOREIGN PATENT DOCUMENTS

| WO | WO 2006/035416 | 4/2006 |
|---|---|---|
| WO | WO 2006/110802 | 10/2006 |
| WO | WO 2005/048998 | 1/2007 |
| WO | WO 2007/012478 | 2/2007 |
| WO | WO 2007/014445 | 2/2007 |
| WO | WO 2007/018943 | 2/2007 |
| WO | WO 2007/095092 | 8/2007 |

OTHER PUBLICATIONS

Liu et al., "Gelatin-Stabilised Microemulsion-Based Organogels Facilitates Percutaneous Penetration of Cyclosporin A In Vitro and Dermal Pharmacokinetics In Vivo," *Journal of Pharmaceutical Sciences* 96(11):3000-3009, Nov. 2007.

Chourasia et al., "Pharmaceutical approaches to colon targeted drug delivery systems," *J. Pharm. Pharmaceut. Sci.* 6(1):33-66-2003.

Gao et al., "Physiochemical characterization and evaluation of a microemulsion system for oral delivery of cyclosporin A," *International Journal of Pharmaceutics* 161:75-86, 1998.

Kim et al., "Once-a-Day Oral Dosing Regimen of Cyclosporin A: Combined Therapy of Cyclosporin A Premicroemulsion Concentrates and Enteric Coated Solid-State Premicroemulsion Concentrates," *Pharmaceutical Research* 18(4):454-459, 2001.

Final Office Action dated Jun. 17, 2011, from U.S. Appl. No. 11/663,834, filed Mar. 27, 2007.

Non-Final Office Action dated Jul. 15, 2011, from U.S. Appl. No. 11/236,549, filed Sep. 28, 2005.

Al-Meshal et al., "Oral administration of liposomes containing cyclosporine: a pharmacokinetic study," *International Journal of Pharmaceutics* 168:163-168, 1998.

Anderberg et al., "Sodium Caprate Elicits Dilatations in Human Intestinal Tight Junctions and Enhances Drug Absorption by the Paracellular Route," *Pharmaceutical Research* 10(6):857-864, 1993.

Barnes et al., "Theophylline: New Perspectives for an Old Drug," *AM J Respir Crit Care Med* 167:813-818, 2003.

Borel et al., "Carotenoids in biological emulsions: solubility, surface-to-core distribution, and release from lipid droplets," *Journal of Lipid Research* 37:250-261, 1996.

Chowdary et al., "Controlled Nifedipine Release from Microcapsules of its Dispersions in PVP-MCC and HPC-MCC," *Drug Development and Industrial Pharmacy* 21(10):1183-1192, 1995.

Drewe et al., "The absorption site of cyclosporine in the human gastro-intestinal tract," *Br. J. clin. Pharmac.* 33:39-43, 1992.

Gursoy et al., "Self-emulsifying drug delivery systems (SEDDS) for improved oral delivery of lipophilic drugs," *Biomedicine & Pharmacotherapy* 58:173-182, 2004.

Ikegawa et al., Inhibition of P-glycoprotein by flavonoid derivatives in Adriamycin-resistant human myelogenous leukemia (K562/ADM)cells, *Cancer Letters* 177:89-93, 2002.

Manakova et al., "Failure of FK506 (tacrolimus) to alleviate apomorphine-induced circling in rat Parkinson model in spite of some cytoprotective effects in SH-SY5Y dopaminergic cells," *Brain Research* 1038:83-91, 2005.

McGinity et al., Aqueous Polymeric Coatings for Pharmaceuticals Dosage Forms, *Marcel Dekker, Inc.*, 1997.

Miller et al., "Controlled Trial of Nimodipine in Amyotrophic Lateral Sclerosis," *Neuromusc. Disord.*, 6(2):101-104, 1996.

Ribeiro et al., "Microencapsulation of lipophilic drugs in chitosan-coated alginate microspheres," *International Journal of Pharmaceutics* 187:115-123, 1999.

Strowig et al., Comparison of Insulin Monotherapy and Combination Therapy with Insulin and Metformin or Insulin and Troglitazone in Type 2 Diabetes, *Diabetes Care* 25(10):1691-1698, 2002.

Sweetman and Martindale, "Nimodipine," *Cardiovascular Drugs* p. 946, 2002.

Yang et al., "Transport and uptake characteristics of a new derivative of berberine (CPU-86017) by human intestinal epithelial cell line: Caco-2," *Acta Pharmacol Sin* 24(12):1185-1191, 2003.

Yeh et al., "Effect of Medium-Chain Glycerides on Physiological Properties of Rabbit Intestinal Epithelium in Vitro," *Pharmaceutical Research* 11(8):1148-1154, 1994.

Zhang et al., "P-glycoprotein restricted transport of nimodipine across blood-brain barrier," *Acta Pharmacol Sin* 24(9):903-906, 2003.

Zuber et al., "Reversible cerebral angiopathy," *J Neurol* 253:1585-1588, 2006.

Non-Final Office Action from U.S. Appl. No. 11/236,549 dated May 5, 2009.

Non-Final Office Action from U.S. Appl. No. 11/236,549 dated Oct. 6, 2010.

Non-Final Office Action from U.S. Appl. No. 11/663,834 dated Mar. 3, 2010.

Non-Final Office Action dated Jun. 21, 2012, from corresponding U.S. Appl. No. 12/597,154.

Milojevic et al., "Amylose as a coating for drug delivery to the colon: Preparation and in vitro evaluation using 5-aminosalicylic acid pellets," *Journal of Controlled Release* 38:75-84, 1996.

Murthy et al., "Treatment of Dextran Sulfate Sodium-Induced Murine Colitis by Intracolonic Cyclosporin," *Digestive Diseases and Sciences* 38(9):1722-1734, Sep. 1993.

Non-final Office action from U.S. Appl. No. 12/594,534, dated Mar. 30, 2012, 31pp.

Non-final Office action from U.S. Appl. No. 12/598,395, dated Mar. 26, 2012, 11pp.

Final Office action from U.S. Appl. No. 11/236,549, dated Mar. 15, 2012, 25pp.

Madene et al., "Flavour encapsulation and controlled release—a review," *International Journal of Food Science and Technology* 41:1-21, 2006.

Non-Final Office Action from co-pending U.S. Appl. No. 12/594,542 dated Oct. 5, 2012.

Non-Final Office Action from co-pending U.S. Appl. No. 13/321,149 dated Nov. 9, 2012.

Non-Final Office Action from co-pending U.S. Appl. No. 13/441,780 dated Nov. 28, 2012.

Feagan et al., "Low-Dose Cyclosporine for the Treatment of Crohn's Disease," *The New England Journal of Medicine*, 330(26):1846-1851, Jun. 30, 1994.

French et al., "Evaluation of the Physiochemical Properties and Dissolution Characteristics of Mesalamine: Relevance to Controlled Intestinal Drug Delivery," *Pharmaceutical Research* 10(9):1285-1290, 1993.

McGinity et al., "Enteric Film Coating of Soft Gelatin Capsules," *Drug Development & Delivery* 3(6), Sep. 6, 2003.

Qiu et al., "Developing Solid Oral Dosage Forms: Pharmaceutical Theory & Practice," *Academic Press* p. 445 only, 2009.

Reich, "Formulation and physical properties of soft capsules," Chapter 11, *Pharmaceutical Capsules*, $2^{nd}$ edition, Edited by Fridrun Podczeck and Brian E Jones, p. 208, 2004.

van Deventer, "Small therapeutic molecules for the treatment of inflammatory bowel disease," *Gut* 50(Suppl III): iii47-iii53, 2002.

Drug Bank, www.drugbank.ca/drugs/DB00244, 12 pages.

Rodriguez et al., "Colonic budesonide delivery from ph-dependent microcapsules containing lipidic cores," *Acta Technologiae et Legis Medicamenti* XI(1):45-52, 2000.

Klausner et al., "Expandable gastroretentive dosage forms," *Journal of Controlled Release* 90:143-162, 2003.

Dhara et al., "Stability of Sodium Dodecyl Sulfate Micelles in the Presence of a Range of Water-Soluble Polymers: A Pressure-Jump Study," *J Phys. Chem. B.*, 105: 7133-7138; 2001.

Greener et al., "Interaction of Anionic Surfactants with Gelatin: Viscosity Effects," *Macromolecules*, 20: 2490-2498; 1987.

Holmberg et al., *Surfactants and Polymers in Aqueous Solution*. John Wiley & Sons, Ltd. 2002.

Muller et al. "Competitive Adssorption of Gelatin and Sodium Dodecylbenzenesulfonate at Hydrophobic Surfaces," *Langmuir*, 14: 3107-3114; 1998.

(56) References Cited

OTHER PUBLICATIONS

Wesley et al., "Structure of Polymer/Surfactant Complexes Formed by Poly(2-(dimethylamino)ethyl metharylate) and Sodium Dodecyl Sulfate," *Langmuir* 18: 5704-5707; 2002.

Shioji, Yusaku, "Manufacturing technology of solid formulation", CMC publishing Co. Ltd., pp. 46-48 and 174-177, Jan. 27, 2003.

Office Action, for Japanese Patent Application No. 2006-507572, Sep. 24, 2014.

* cited by examiner

PHARMACEUTICAL COMPOSITION OF TACROLIMUS

CROSS REFERENCE TO RELATED APPLICATIONS

This is the U.S. National Stage of International Application No. PCT/IE2008/000039, filed Apr. 4, 2008, which was published in English under PCT Article 21(2), which in turn claims the benefit of U.S. Provisional Application No. 60/907,490, filed Apr. 4, 2007, and U.S. Provisional Application No. 61/006,498, filed Jan. 16, 2008. The provisional applications are incorporated herein in their entirety.

The present invention relates to pharmaceutical compositions comprising Tacrolimus.

INTRODUCTION

Tacrolimus, a macrolide agent, inhibits T-lymphocyte activation through a process that is thought to involve it binding to an intracellular protein, FKBP-12. A hydrophobic complex of tacrolimus-FKBP-12, calcium, calmodulin, and calcineurin is then formed and the phosphatase activity of calcineurin inhibited. This effect may prevent the dephosphorylation and translocation of nuclear factor of activated T-cells (NF-AT), a nuclear component thought to initiate gene transcription for the formation of lymphokines (such as interleukin-2, gamma interferon). The resulting inhibition of T-lymphocyte activation leads to potent immunosuppression (Prograf® Patient Information Brochure (Astellas)).

Tacrolimus is primarily used in post-organ transplant patients to prevent organ rejection. One week after organ transplant, the tacrolimus dose is adjusted to maintain whole blood trough concentrations of tacrolimus within the target range (10-20 ng/ml during the first 3 months and 5-15 ng/ml thereafter (Yasuhara et al., (1995) Transplantation Proceedings, 27, 1108-1110). The majority of patients can be successfully managed if the trough (12 hour) blood concentrations are maintained within the following range: For liver transplant the effective range is 5-20 ng/mL for the first 3 month, 5-15 ng/mL thereafter; for kidney transplant the effective range is 10-20 ng/mL for the first 3 months, 5-15 ng/mL thereafter; for heart transplant the effective range is 10-20 ng/mL for the first 3 months, 5-15 ng/mL thereafter; and for lung transplant the effective range is 10-20 ng/mL for the first month, then 5-15 ng/mL thereafter. The onset of organ rejection was found to be associated with a lower blood concentration while adverse effects occurred at a blood concentration higher than 15 ng/ml (Masuda et al., (2006) Pharmacology and Therapeutics, 112, 184-198).

Tacrolimus is differentially absorbed from in different regions of the gastrointestinal tract, being optimally absorbed from the small intestine, with ileum and colonic absorption efficiency dropping to half that observed for the small intestine. Also, a food effect is observed. After absorption from the gastrointestinal tract, drug effects persist for 8-12 hours after oral administration of conventional IR tablets. The total dosage is typically in the range of 2.5-10 mg per day, in exceptional cases rising to 20 mg/day. Under conventional dosage regimes, Tacrolimus is given twice daily, typically with one dose given before breakfast and a second dose given in the late afternoon. Adverse effects, due to the initial rapid absorption from the small intestine results in above therapeutic plasma concentrations, associated with tacrolimus treatment include nephrotoxicity, neurotoxicity and the development of patient infection due to immunosuppression.

A once-daily formulation of tacrolimus is known. The formulation process consists of tacrolimus being granulated with dehydrated ethanol, ethylcellulose, hypromellose and lactose monohydrate. The hypromellose system modifies the drug release profile by forming a polymer gel layer and the ethylcellulose diffusion matrix system modifies the release profile by controlling water penetration and thus drug release. The resulting paste undergoes drying and sizing to produce intermediate granules. The granules are then mixed with lactose monohydrate and magnesium stearate and that mixture is filled into capsules. The formulation results in dissolution of 90% drug release at 6 to 12 hours. One potential problem with this once-daily product results in an initial spike in the drug plasma concentration, with the potential to cause unwanted side effects.

There is, therefore, a need for an improved composition of Tacrolimus that will address at least some of these issues.

STATEMENTS OF INVENTION

According to the invention there is provided an oral tacrolimus composition comprising minicapsules having a core containing tacrolimus in a solubilised liquid form, the minicapsules having a release profile to release the pre-solubilised tacrolimus throughout the entire gastrointestinal tract.

In one embodiment the minicapsules have a release profile to release pre-solubilised tacrolimus in the small intestine.

In one embodiment the minicapsules have a release profile to release pre-solubilised tacrolimus in the ileum.

In one embodiment the minicapsules have a release profile to release pre-solubilised tacrolimus in the colon.

In one case tacrolimus is present in the core in an amount of from 0.5 to 25% w/w, preferably in an amount of from 2.5 to 15% w/w.

In one embodiment when exposed to a use environment less than 30% of the tacrolimus is released within 1 hour, preferably when exposed to a use environment less than 20% of the tacrolimus is released within 1 hour.

In one embodiment when exposed to a use environment less than 60% of the tacrolimus is released within 4 hours, preferably when exposed to a use environment less than 35% of the tacrolimus is released within 4 hours.

In one embodiment when exposed to a use environment less than 90% of the tacrolimus is released within 12 hours, preferably when exposed to a use environment less than 65% of the tacrolimus is released within 12 hours.

In one case when exposed to a use environment less than or equal to 100% of the tacrolimus is released within 24 hours.

In one embodiment when exposed to a use environment less than 20% of the tacrolimus is released within 1 hour, less than 35% of the tacrolimus is released within 4 hours, less than 65% of the tacrolimus is released within 12 hours, and substantially all of the remaining tacrolimus is released between 12 and 24 hours.

The minicapsules may comprise a solid shell containing the solubilised tacrolimus. The minicapsules may be modified to provide the release profile. A modified release may be attributable to a polymer coating. The polymeric material may, for example, be a methacrylate, or ethylcellulose. The polymeric material may be a composite of methacrylate and ethylcellulose.

In one embodiment the coating includes a dissolution enhancing agent. The dissolution enhancing agent may be degraded by bacteria normally present in the gastrointestinal tract. The dissolution enhancing agent may be selected from one or more of pectin, amylose and alginate. The dissolution enhancing agent can be present in an amount of from 0.5 to 2% w/w of ethylcellulose.

In one embodiment the core comprises tacrolimus, a solubilisation agent, a co-emulsifier, a surfactant, a permeability enhancer and a carrier. The solubilisation agent may comprise ethanol. The solubilisation agent may comprise triglycerides. The co-emulsifying agent may comprise fatty acid ester complexes. The surfactant agent may comprise fatty acid ester complexes. The permeability enhancing agent may comprise fatty acid ester complexes. The carrier may comprise a hydrophobic liquid. The hydrophobic liquid may comprise an oil such as olive oil.

In one embodiment the composition comprises a first population of minicapsules comprising tacrolimus and a second population of minicapsules comprising tacrolimus. The first population may comprise uncoated minicapsules. The second population may comprise coated minicapsules.

In one embodiment the composition comprises from 10 to 40% w/w uncoated minicapsules and from 60 to 90% w/w coated minicapsules.

In one case there are about 25% w/w of uncoated minicapsules and about 75% w/w of coated minicapsules.

In one embodiment tacrolimus is released along the gastrointestinal tract in a form that maximises systemic absorption.

The tacrolimus may be released along the gastrointestinal tract in a form that maximises pre-systemic mucosal absorption.

The tacrolimus may be released along the gastrointestinal tract in a form that maximises local gastrointestinal activity.

Tacrolimus may be released along the gastrointestinal tract in a form that maximises chronotherapy.

In one embodiment the formulation contains an adhesive entity such as a muco- or bio-adhesive.

The minicapsules may be administered in a hard gelatine capsule, a sprinkle, or a tablet.

In one embodiment the minicapsules further comprise excipients to maximise the solubility of tacrolimus. The composition may comprise excipients to maximise permeability of tacrolimus in the ileum. The ileum permeability enhancing excipients may be selected from one or more of:—sodium caprate, sodium dodecanoate, sodium palmitate, SNAC, chitosan and derivatives thereof, fatty acids, surfactants, liposomes, triglycerides, polyethers, bile salts, nitric oxide donors, triglycerides, hydroxylase inhibitors and/or antioxidants.

In another embodiment the composition comprises excipients to maximise permeability of tacrolimus in the colon. The colon permeability enhancing excipients may be selected from one or more of:—sodium caprate, sodium dodecanoate, sodium palmitate, SNAC, chitosan and derivatives thereof, fatty acids, surfactants, liposomes, triglycerides, polyethers, bile salts, nitric oxide donors, triglycerides, hydroxylase inhibitors and/or antioxidants.

The composition may comprise excipients to enhance the therapeutic potential of tacrolimus in the ileum and colon. The excipients may be selected from one or more of absorption limiters, absorption enhancers, surfactants, co-surfactants, co-solvents, essential oils such as omega 3 oils, natural plant extracts such as neem, ion-exchange resins, bacteria degradable conjugation linkers such as azo bonds, polysaccharides such as amylose, guar gum, pectin, chitosan, inulin and cyclodextrins.

In one embodiment the composition comprises excipients to enhance systemic bioavailability of tacrolimus following absorption throughout the gastrointestinal tract. The excipients to enhance systemic bioavailability of tacrolimus following absorption in the small intestine may comprise efflux pump inhibitors, including, PgP pump inhibitors, and metabolism inhibitors, including, cytochrome P450 3A inhibitors.

The composition may also comprise excipients to reduce systemic side effects associated with absorption of tacrolimus in the small intestine. The excipients to reduce systemic side effects associated with absorption of tacrolimus in the small intestine may comprise, antioxidants, such as curcuminoids, flavanoids or more specifically including curcumin, beta-carotene, α-tocopherol, ascorbate or lazaroid.

The composition facilitates absorption over 24 hours.

The composition may be used for the treatment or prevention of solid organ transplant rejection; for the treatment or prevention of graft-versus-host disease; for the treatment or prevention of gastro-intestinal graft-versus-host disease; in treating or preventing inflammatory bowel disease; in treating or preventing ulcerative colitis; in treating or preventing Crohn's disease.

The composition may be combined with another active pharmaceutical ingredient in a single oral dosage form.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION

Figure 1:
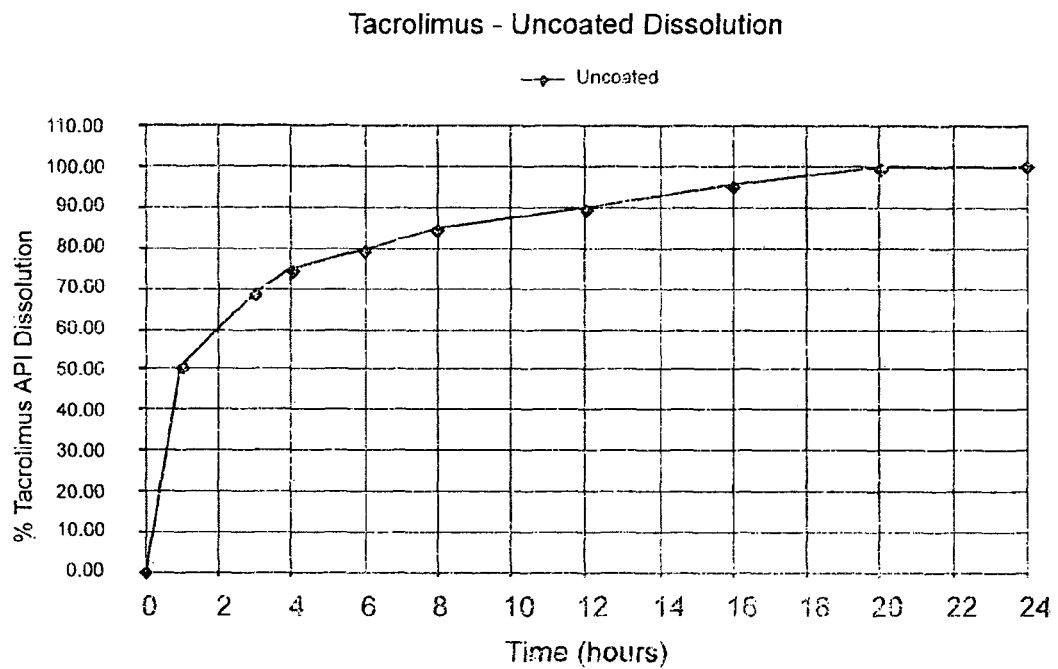
FIG. 1 is a graph showing the dissolution profile for uncoated tacrolimus minicapsules.

The invention provides a once-daily formulation of tacrolimus. The composition provides a controlled release of a therapeutically effective amount of tacrolimus in combination with a pharmaceutically acceptable carrier(s) or excipient(s). The resulting 24-hour controlled release will enable an improved pharmacokinetic profile leading to a potentially more effective, safer and convenient product.

The controlled release of active pharmaceutical agents is only truly useful if the agent is available to interact with its receptor or site of action in an active form. Unless the agent is in a fully soluble form it is unlikely to interact with its intended receptor or exert its desired action. The invention is a drug delivery format that enables the release of tacrolimus from the format in soluble or readily-soluble form.

As the invention permits the release of tacrolimus in soluble or readily-soluble for, it thus enables a true once-daily drug formulation, especially for a small molecule drug with poor water-solubility, possibly with limited stability or a short half-life such as tacrolimus, as the drug is absorbed not only in the small intestine but also in the colon.

The invention provides an oral drug delivery technology that permits throughout the entire gastrointestinal tract the release of pre- or readily-solubilised drugs in tandem with a controlled release formulation that permits release and absorption in the small intestine, ileum and/or colon of soluble tacrolimus to ensure true once-daily formulations which is an hydrophobic agent that has demonstrated variable bioavailability.

In addition to enabling once-daily delivery of tacrolimus throughout the entire gastrointestinal tract for the improved management of post-transplant organ rejection as well as for autoimmune diseases, the development of a colon-specific release formulation is advantageous as an effective drug delivery mechanism for the enhanced treatment of diseases of colon (including, but not limited to, ulcerative colitis, Chron's disease, Gastro-Intestinal Graft Versus Host Disease (GI-GVHD), Irritable Bowel Syndrome) whereby high local concentration can be achieved while minimizing side effects that occur because of release of drugs in the upper GIT or unnecessary systemic absorption.

Traditional dosage forms in which an immediate release (IR) dosage form is administered at periodic intervals typically gives rise to a pulsatile plasma profile, related to the time of ingestion and usually within a short period following such ingestion. Where release from the dosage form is rapid or 'immediate', the peak in the plasma drug concentration is observed after administration of each IR dose with troughs or low plasma concentrations obvious between consecutive administration time points. The pulsatile plasma profiles resulting from such dosage regimes may affect the pharmacological and therapeutic effect, thereby resulting in beneficial or detrimental consequences for certain drug therapies. In some instances, the fall off of the plasma concentration of the active ingredient between peaks results in a wash-out period and may contribute to a reduction in or prevention of patient tolerance to various types of drugs. Pulsatile release formats have proven successful for a range of drugs but many others have not benefited from such delivery systems and it has not been particularly successful for colon-specific or the development of true once-daily forms of certain drug classes, including low solubility small molecules and biopharmaceuticals.

Tacrolimus is an example of a drug that has demonstrated limited colonic absorption.

There is a need for a controlled release format that prevents toxic side effects while enhancing absorption from the entire gastrointestinal tract, including the small intestine, the ileum and colon.

As the above cited tacrolimus examples have proven difficult to formulate, true once-daily formats have proven difficult to develop. To overcome this issue, enhanced delivery systems with the potential to combine aspects of any of solubility, permeability and stability enhancement along with gastro-intestinal targeted release are required.

Additionally, for conditions that may affect the entire gastro-intestinal tract, including the small intestine, such as Crohn's Disease and GI-GVHD, a sustained release format of pre-solubilised Tacrolimus, exhibiting limited systemic absorption is desirable.

As tacrolimus blocks T-cell activation, a prerequisite for HIV proliferation, it may be useful as a prophylactic for the prevention of HIV replication. In the particular cases of HIV-1, HIV-2 and related retroviral strains, inhibition of T-cell mitosis would suppress the replication of the virus, since the virus relies upon the host T-cell's proliferative functions to replicate. The formulations in the invention would be useful when used alone, or in combination therapy with other immunosuppressants and anti-retroviral agents, for example, but not limited to, cyclosporine, rapamycin, picibanil, mycophenolic acid, azathioprine, prednisolone, cyclophosphamide, brequinar, sequinivir and leflunomide as a prophylactic for the prevention of HIV replication which is rapid in the gastrointestinal tract following infection. In the particular cases of HIV-1, HIV-2 and related retroviral strains, inhibition of T-cell mitosis would suppress the replication of the virus, since the virus relies upon the host T-cell's proliferative functions to replicate.

As an immunosuppressants, the tacrolimus formulations, alone or in combination with other actives, are useful when administered for the prevention of immune-mediated tissue or organ graft rejection. Examples of transplanted tissues and organs which suffer from these effects are heart, kidney, liver, medulla ossium, skin, cornea, lung, pancreas, intestinum tenue, limb, muscle, nervus, duodenum, small-bowel, pancreatic-islet-cell, and the like; as well as graft-versus-host diseases brought about by medulla ossium transplantation. The regulation of the immune response by the formulations of the invention would also find utility in the treatment of autoimmune diseases, such as rheumatoid arthritis, systemic lupus erythematosis, hyperimmunoglobulin E, Hashimoto's thyroiditis, multiple sclerosis, progressive systemic sclerosis, myasthenia gravis, type 1 diabetes, uveitis, allergic encephalomyelitis, glomerulonephritis, and the like; and further infectious diseases caused by pathogenic microorganisms, such as HIV (Human Immunodeficiency Virus). In the particular cases of HIV-1, HIV-2 and related retroviral strains, inhibition of T-cell mitosis would suppress the replication of the virus, since the virus relies upon the host T-cell's proliferative functions to replicate.

Further uses for the current invention formulations, alone or in combination with other actives, include the treatment and prophylaxis of inflammatory and hyperproliferative skin diseases and cutaneous manifestations of immunologically-mediated illnesses, such as psoriasis, atopic dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, *Lupus erythematosus*, acne and Alopecia greata; various eye diseases (autoimmune and otherwise) such as keratoconjunctivitis, vernal conjunctivitis, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, multiple myeloma, etc.; obstructive airway diseases, which includes conditions such as COPD, asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis and the like; inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury can be treated or prevented by the compounds of the invention.

Other treatable conditions for the formulations in this invention, alone or in combination with other actives, would include but are not limited to ischemic bowel diseases; necrotizing enterocolitis, intestinal lesions associated with thermal burns and leukotriene B$_4$-mediated diseases; intestinal inflammations/allergies such as Coeliac diseases, proctitis, eosinophilic gastroenteritis, mastocytosis; food-related allergic diseases which have symptomatic manifestation remote from the gastro-intestinal tract (e.g., migraine, rhinitis and eczema); renal diseases such as interstitial nephritis, Goodpasture's syndrome, hemolytic-uremic syndrome and diabetic nephropathy; nervous diseases such as multiple myositis, Guillain-Barre-syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction) as well as neurodegenerative diseases (for example Parkinson's disease, Alzheimer's disease, vascular dementia and so forth): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis. such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-C$_4$ release; Behcet's disease such as intestinal-, vasculo- or neuro-Behcet's disease, and also Behcet's which affects the oral cavity, skin, eye, vulva, articulation, epididymis, lung, kidney and so on.

Furthermore, the formulations of the invention, alone or in combination with other actives, are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytonegalovirus infection, particularly HCMV (Human Cytomegalovirus infection, anti-inflammatory activity, and so on.

The formulations of the invention, alone or in combination with other actives, may be used as vaccines to treat immunosuppression in a subject. It is sometimes found that the antigen introduced into the body for the acquisition of immunity from disease also acts as an immunosuppressive agent, and therefore, antibodies are not produced by the body and immunity is not acquired. By introducing a formulation of the invention into the body as a vaccine, the undesired immunosuppression may be overcome and immunity acquired.

The formulations of the invention may also find utility in the chemosensitization of drug resistant target cells. Tacrolimus is known to be effective modulators of P-glycoprotein, a substance which binds to and inhibits the action of anticancer drugs by inhibiting P-glycoprotein, as they are capable of increasing the sensitivity of multidrug resistant (MDR) cells to chemotherapeutic agents. It is believed that the formulations of the invention may likewise be effective at overcoming resistance expressed to clinically useful antitumour drugs such as 5-fluorouracil, cisplatin, methotrexate, vincristine, vinblastine and adriamycin, colchicine and vincristine.

The invention enables the formulation of tacrolimus in a solid form. Liquid dosage forms for oral administration include pharmaceutically-acceptable emulsions, solutions, suspensions, syrups and elixirs. In addition to the active cyclosporine, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, the Labrafil™ range, Labrafrac™ range, Gelucire™ range, oils (in particular, cottonseed, groundnut, corn, germ, olive, castor, fish, neem and sesame oils), polyethers (in particular substances like dimethyl isosorbide, dimethyl isoodide and dimethly isomannide and mixtures of glyceryl monoesters of C8-C22 fatty acids and hexaglyceryl to pentadecaglyceryl monoesters of C8-C22 fatty acids in variable ratios from 1:3 to 1:8), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Liquid formulations may contain, in addition to the active compounds, suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

The invention allows for a broad range of controlled release polymer coatings to be applied. Coating materials may include any combination of the commercially available acrylic-, methacrylic-, ethylcellulose-based polymers (such as, but not limited to the Eudragit™ and Surelease® range), as well as other polymers with natural polysaccharides, including, but not limited to amylose, pectin, alginate, amylopectin, chitosan, galactomannan, guar gum and any derivatives thereof, has the potential to customise how, where and when drugs are released from the underlying or embedded solid, semi-solid or liquid forms. In all examples cited in this specification, any specific polymer may be interchanged or combined with any other polymer to enable the required release profile according to the preferred optimal therapeutic outcome envisaged.

In various embodiments comprising a membrane-controlled dosage form, the polymeric material comprises methacrylic acid co-polymers, ammonio methacrylate co-polymers, or mixtures thereof. Methacrylic acid co-polymers such as EUDRAGIT™ S and EUDRAGIT™ L (Evonik) are suitable for use in the controlled release formulations of the present invention. These polymers are gastroresistant and enterosoluble polymers. Their polymer films are insoluble in pure water and diluted acids. They dissolve at higher pHs, depending on their content of carboxylic acid. EUDRAGIT™ S and EUDRAGIT™ L can be used as single components in the polymer coating or in combination in any ratio. By using a combination of the polymers, the polymeric material can exhibit solubility at a pH between the pHs at which EUDRAGIT™ L and EUDRAGIT™ S are separately soluble.

The membrane coating can comprise a polymeric material comprising a major proportion (i.e., greater than 50% of the total polymeric content) of at least one pharmaceutically acceptable water-soluble polymers, and optionally a minor proportion (i.e., less than 50% of the total polymeric content) of at least one pharmaceutically acceptable water insoluble polymers. Alternatively, the membrane coating can comprise a polymeric material comprising a major proportion (i.e., greater than 50% of the total polymeric content) of at least one pharmaceutically acceptable water insoluble polymers, and optionally a minor proportion (i.e., less than 50% of the total polymeric content) of at least one pharmaceutically acceptable water-soluble polymer.

Ammonio methacrylate co-polymers such as EUDRAGIT™ RS and EUDRAGIT™ RL (Evonik) are suitable for use in the modified release formulations of the present invention. These polymers are insoluble in pure water, dilute acids, buffer solutions, or digestive fluids over the entire physiological pH range. The polymers swell in water and digestive fluids independently of pH. In the swollen state, they are then permeable to water and dissolved active agents. The permeability of the polymers depends on the ratio of ethylacrylate (EA), methyl methacrylate (MMA), and tri-methylammonioethyl methacrylate chloride (TAMCl) groups in the polymer. Those polymers having EA:MMA:TAMCl ratios of 1:2:0.2 (EUDRAGIT™ RL) are more permeable than those with ratios of 1:2:0.1 (EUDRAGIT™ RS). Polymers of EUDRAGIT™ RL are insoluble polymers of high permeability. Polymers of EUDRAGIT™ RS are insoluble films of low permeability.

The amino methacrylate co-polymers can be combined in any desired ratio, and the ratio can be modified to modify the rate of drug release. For example, a ratio of EUDRAGIT™ RS: EUDRAGIT™ RL of 90:10 can be used. Alternatively, the ratio of EUDRAGIT™ RS: EUDRAGIT™ RL can be about 100:0 to about 80:20, or about 100:0 to about 90:10, or any ratio in between. In such formulations, the less permeable polymer EUDRAGIT™ RS would generally comprise the majority of the polymeric material with the more soluble RL, when it dissolves, permitting creating gaps through which solutes can enter the core and dissolved pharmaceutical actives escape in a controlled manner.

The amino methacrylate co-polymers can be combined with the methacrylic acid co-polymers within the polymeric material in order to achieve the desired delay in the release of the drug. Ratios of ammonio methacrylate co-polymer (e.g., EUDRAGIT™ RS) to methacrylic acid co-polymer in the range of about 99:1 to about 20:80 can be used. The two types of polymers can also be combined into the same polymeric material, or provided as separate coats that are applied to the core.

Eudragit™ FS 30 D is an anionic aqueous-based acrylic polymeric dispersion consisting of methacrylic acid, methyl acrylate, and methyl methacrylate and is pH sensitive. This polymer contains fewer carboxyl groups and thus dissolves at a higher pH (>6.5). The advantage of such a system is that it can be easily manufactured on a large scale in a reasonable processing time using conventional powder layering and fluidized bed coating techniques. In a study by Gupta et al (*Int J Pharm*, 213: 83-91, 2001) Eudragit FS 30 D demonstrated its potential for colonic delivery by resisting drug release up to pH 6.5 and the combination of Eudragit™ RL and RS proved successful for the sustained delivery of 5-ASA at the pH of the colon. Thus, Eudragit™ FS 30 D alone or with other controlled release polymers holds great potential to enable delivery of minicapsule formulations specifically to the colon.

In addition to the EUDRAGIT™ polymers described above, a number of other such copolymers can be used to control drug release. These include methacrylate ester co-polymers such as the EUDRAGIT™ NE and EUDRAGIT™ NM ranges. Further information on the EUDRAGIT™ polymers can be found in "Chemistry and Application Properties of Polymethacrylate Coating Systems," in Aqueous Polymeric Coatings for Pharmaceutical Dosage Forms, ed. James McGinity, Marcel Dekker Inc., New York, pg 109-114.

Several derivatives of hydroxypropyl methylcellulose (HPMC) also exhibit pH dependent solubility. Shin-Etsu Chemical Co., Ltd. esterified HPMC with phthalic anhydride to produce hydroxypropyl methylcellulose phthalate (HPMCP), which rapidly dissolves in the upper intestinal tract. Due to the limited compatibility of HPMCP with several types of plasticizers, hydroxypropyl methylcellulose acetate succinate (HPMCAS) was developed. The presence of ionizable carboxyl groups in the HPMCAS structure cause the polymer to solubilize at high pH (>5.5 for the LF grade and >6.8 for the HF grade). This polymer exhibits good compatibility with a variety of plasticizing agents and is commercially available from Shin-Etsu Chemical Co. Ltd. under the proprietary name AQOAT® in a powdered form to be redispersed in water.

Surelease® dispersion is a unique combination of film-forming polymer; plasticizer and stabilizers. Designed for sustained release and taste masking applications, Surelease is an easy-to-use, totally aqueous coating system using ethylcellulose as the release rate controlling polymer. The dispersion provides the flexibility to adjust drug release rates with reproducible profiles that are relatively insensitive to pH. The principal means of drug release is by diffusion through the Surelease dispersion membrane and is directly controlled by film thickness. Increasing or decreasing the quantity of Surelease® applied can easily modify the rate of release. With Surelease dispersion, reproducible drug release profiles are consistent right through from development to scale-up and production processes.

In addition to the EUDRAGIT™ and Surelease® polymers discussed above, other enteric, or pH-dependent, polymers can be used. Such polymers can include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropyl-methylcellulose phthalate, hydroxypropylmethylcellulose acetate succinate, starch acetate phthalate, amylose acetate phthalate, polyvinyl acetate phthalate, and polyvinyl butyrate phthalate. Additionally, where compatible, any combination of polymer may be blended to provide additional controlled- or targeted-release profiles.

The coating membrane can further comprise at least one soluble excipient to increase the permeability of the polymeric material. Suitably, the at least one soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as sodium lauryl sulfate and polysorbates, organic acids such as acetic acid, adipic acid, citric acid, fumaric acid, glutaric acid, malic acid, succinic acid, and tartaric acid, sugars such as dextrose, fructose, glucose, lactose, and sucrose, sugar alcohols such as lactitol, maltitol, mannitol, sorbitol, and xylitol, xanthan gum, dextrins, and maltodextrins. In some embodiments, polyvinyl pyrrolidone, mannitol, and/or polyethylene glycol can be used as soluble excipients. The at least one soluble excipient can be used in an amount ranging from about 1% to about 10% by weight, based on the total dry weight of the polymer. The coating process can be carried out by any suitable means, for example, by using a perforated pan system such as the GLATT, ACCELACOTA, Vector, Diosna, O'Hara, HICOATER or other such coating process equipment. Seamless minicapsules may be manufactured using the method described in U.S. Pat. No. 5,882,680 (Freund), the entire contents of which are incorporated herein by reference.

The modifications in the rates of release, such as to create a delay or extension in release, can be achieved in any number of ways. Mechanisms can be dependent or independent of local pH in the intestine, and can also rely on local enzymatic activity to achieve the desired effect. Examples of modified-release formulations are known in the art and are described, for example, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566.

A number of modified dosage forms suitable for use are described below. A more detailed discussion of such forms can also be found in, for example The Handbook of Pharmaceutical Controlled Release Technology, D. L. Wise (ed.), Marcel Decker, Inc., New York (2000); and also in Treatise on Controlled Drug Delivery: Fundamentals, Optimization, and Applications, A. Kydonieus (ed.), Marcel Decker, Inc., New York, (1992), the relevant contents of each of which are hereby incorporated by reference for this purpose. Examples of modified-release formulations include but are not limited to, membrane-modified, matrix, osmotic, and ion-exchange systems. All of these can be in the form of single-unit or multi-unit dosage forms, as alluded to above.

With membrane-modified extended-release dosage forms, a semi-permeable membrane can surround the formulation containing the active substance of interest. Semi-permeable membranes include those that are permeable to a greater or lesser extent to both water and solute. This membrane can include water-insoluble and/or water-soluble polymers, and can exhibit pH-dependent and/or pH-independent solubility characteristics. Polymers of these types are described in detail below. Generally, the characteristics of the polymeric membrane, which may be determined by, e.g., the composition of the membrane, will determine the nature of release from the dosage form.

In particular, the present invention provides for formulations of minicapsules or minispheres wherein the modified release is dependent upon, where appropriate, any one of the core formulation constituents, the shell composition or the shell coating. The minicapsules or minispheres may be produced through the utilisation of surface tension of one or more different solutions which when ejected through an orifice or nozzle with a certain diameter and subject to specific frequencies and gravitational flow, forms into a spherical form and falls into a cooling air flow or into a cooling or hardening solution and the outer shell solution where it is gelled or solidified. This briefly describes the formation of seamless minispheres. According to prior art the core solution is mainly a hydrophobic solution or suspension. The outer shell solution can be any gel forming agent but is normally gelatine- or alginate-based based but may also include polymers or other materials that enable controlled release. However a hydrophilic solution can also be encapsulated with the existence of an intermediate solution, which can avoid the direct contact of the hydrophilic core solution with the outer shell. With the nozzle having a single orifice, a minicapsule or a bead of shell/core mixed suspension can be processed. With the nozzle having two orifices (centre and outer), a hydrophobic solution can be encapsulated. Where appropriate, it may be possible that both the core and/or shell may be comprised of a material or material composites that have been processed by a wet- or dry-extrusion mechanism, melt or otherwise fluidized prior to mixing or extrusion. Ideally, to enable drug content and release consistency, it is preferred that all processes will result in fairly uniform morphologies with a relatively smooth surface to facilitate quite even coating layers to be added in a uniform manner. With the nozzle having one or more orifices seamless minicapsules for various applications can be processed using minicapsule processing equipment enabled by, but not limited to, Freund Spherex, ITAS/Lambo Globex or Inotech processing equipment. As outlined above the coating process can be carried out by any suitable means, for example, by using a perforated pan or fluidized-based system such as the GLATT, Vector, ACCELACOTA, Diosna, O'Hara and/or HICOATER processing equipment.

The result is modified release compositions that in operation deliver one or more active ingredients in a unique, bimodal or multimodal manner. The present invention further relates to solid oral dosage forms, sachets or other orally deliverable formats containing such multiple minicapsule or minisphere controlled release compositions as well as methods for delivering one or more active ingredients to a patient in a bimodal or multimodal manner. Furthermore, the invention permits targeted release of orally delivered formulations to specific regions of the gastrointestinal tract to maximize absorption, confer protection on the payload, to optimize treatment of diseased intestinal tissue or enhance oral bioavailability. Additionally, the invention enables one or more pharmaceutical active to be administered sequentially or concomitantly to improve disease treatment and management and to benefit from the body's natural circadian rhythms. The invention also permits the release of pharmaceutical actives into the ileum and colon for the enhanced treatment of local intestinal diseases or to facilitate the absorption of active pharmaceutical agents, including biopharmaceuticals such as peptide and proteins.

In the invention, for drugs where systemic bioavailability is critical, that transport of the active agent from the intestinal or colonic lumen to the blood or lymphatic system is maximized. As the physicochemical properties of drugs vary widely absorption of different drug classes, from hydrophilic, hydrophobic to lipophilic, are absorbed to varying extents as they pass along the gastrointestinal tract from stomach to colon. In general, the more lipophilic agents are more readily absorbed from the entire intestine than are hydrophilic agents. Where lipophilic agents exhibit poor permeability they are often formulated as micro- or other emulsions that permit interaction with bile salts which enhances absorption in the small intestine. To enhance hydrophilic intestinal permeability various approaches have been adopted, including the development of lipid-based conjugates which confer upon the active agent a more lipid-like nature which permits enhanced small intestinal permeability and hence systemic bioavailability. The potential applications include, but are not limited to, anticancer agents to target metastatic cancerous cells in the lymphatic system, vaccines, immunomodulators, including immunostimulators, agents that undergo extensive first-pass effects in the liver, as well as to enhance the relative half-live of active pharmaceuticals in patients with short bowels and where absorption is limited to the intact small intestine. Where the absorption of small molecules with limited half-lives that are systemically absorbed only through the small intestine is required, the development of controlled release floating systems, whereby the system, in this instance controlled-release multiple minicapsules, is buoyant in the gastric environment may be enabled by this invention.

The invention relates to drug delivery in the colon which has been largely overlooked from a drug delivery perspective. Mainly having evolved to regulate electrolyte balance and to further breakdown complex carbohydrate structures there is a significant flow of water from the colonic lumen into the body. In addition, the colon is home to a natural bacterial flora to degrade complex carbohydrates to ensure effective excretion, provide much needed fibre and some nutrient absorption. With a much lower concentration of proteolytic and other enzymes populated in the colon, it is a much more benign environment for proteins and peptides as well as other biological entities such as carbohydrates and nucleic acids. From a drug delivery perspective, the colon presents a number of interesting possibilities: the bacteria can be harnessed to break down controlled release coatings that are resistant to acidic breakdown as well as pH differentials; the benign environment ensure than active pharmaceuticals, including biopharmaceuticals, are less likely to be degraded if released locally into the colon; the almost continuous flow of fluids from the colonic lumen to the bloodstream may be harnessed to carry hydrophilic entities from the intestine to the lumen. Finally, the long transit time in the colon, ranging form 10-20 hours provides greater residence and potential for interaction with the colonic mucus and epithelial cells leading to enhanced absorption.

Technologically, this invention is based on various modifications of basic one- or multi-layered minicapsules, modulating the core, the shell or the coating to permit enhanced solubility and permeability of the drug or other active or non-active entity as well as conferring protection on drugs or entities that are susceptible to various forms of intestinal, mucosal or systemic degradation and targeted release of the therapeutically-active or -inactive entities to predetermined regions of the gastrointestinal tract.

In addition to the above minicapsule modifications, the present invention provides the coating of minicapsules or minispheres with a muco- or bio-adhesive entity which will ensure that they first adhere to the mucosa prior to releasing the fragile payload. The advantages thus enabled include further protection of the active entities but also release of the actives proximal to the site of absorption. As absorption is, in part, related to the surface area exposed to the active as well as the concentration gradient from intestinal luminal side to the intestinal basal side, the higher local yet dispersed concentration has greater potential to ensure enhanced absorption, not only of hydrophilic drugs, but also lipophilic or hydrophobic drugs.

A barrier to effective colonic delivery of hydrophobic and lipophilic drugs is that the colon did not evolve to solubilize foodstuffs and other entities but rather to ensure electrolyte balance and maximize fibre breakdown and fermentation. The colon remains very porous to hydrophilic entities. By delivering hydrophobic or lipophilic drugs to the colon in a pre-solubilised or readily soluble format and releasing such in the colon, the potential for absorption is enhanced significantly. The present invention permits the encapsulation of pre-solubilized or readily soluble drugs in liquid or hydrolysable semi-solids or solids into the minicapsule core and then modulation of the shell to include intestinal- or colon-controlled release polymers or coating the shell with same. The result is release of optimized formulations at specific sites along the intestinal tract for maximal therapeutic efficacy or systemic absorption.

Likewise, delivery of formulations that are readily broken down in an aqueous environment or a bacteria rich environment has the potential, when coated with colon-specific controlled release polymers or include entities that are degraded by bacteria have the potential to protect susceptible entities from the gastric or intestinal environment yet ensure that they are released intact in the colon where, once liberated, will be readily absorbed. Redox-sensitive, pectin-, alginate-, chitosan- or other bacterially susceptible polymer-based matrices, coatings or other sustained release formulations, liquid, semi-solid or solid, can be encapsulated into or coated onto one- or multi-layered minicapsules.

The formulations of the present invention can exist as multi-unit or single-unit formulations. The term "multi-unit" as used herein means a plurality of discrete or aggregated minicapsules, minispheres, particles, beads, pellets, granules, tablets, or mixtures thereof, for example, without regard to their size, shape, or morphology. Single-unit formulations include, for example, tablets, hard gelatin capsules, caplets, and pills.

The methods and formulations of the present invention are intended to encompass all possible combinations of components that exhibit modified-release and immediate-release properties. For example, a formulation and/or method of the invention can contain components that exhibit extended-release and immediate-release properties, or both delayed-release and immediate-release properties, or both extended-release and delayed-release properties, or a combination of all three properties. For example, a multi-minicapsule or multi-minisphere formulation including both immediate-release and extended-release components can be combined in a capsule, which is then coated with an enteric coat to provide a delayed-release effect. Or, for example, a delayed- and extended-release caplet may comprise a plurality of discrete extended-release particles held together with a binder in the caplet, which is coated with an enteric coating to create a delay in dissolution.

As used herein, the term "modified-release" formulation or dosage form includes pharmaceutical preparations that achieve a desired release of the drug from the formulation. A modified-release formulation can be designed to modify the manner in which the active ingredient is exposed to the desired target. For example, a modified-release formulation can be designed to focus the delivery of the active agent entirely in the distal large intestine, beginning at the cecum, and continuing through the ascending, transverse, and descending colon, and ending in the sigmoid colon. Alternatively, for example, a modified-release composition can be designed to focus the delivery of the drug in the proximal small intestine, beginning at the duodenum and ending at the ileum. In still other examples, the modified-release formulations can be designed to begin releasing active agent in the jejunum and end their release in the transverse colon or rectum. The possibilities and combinations are numerous, and are clearly not limited to these examples.

The term "modified-release" encompasses "extended-release" and "delayed-release" formulations, as well as formulations having both extended-release and delayed-release characteristics. An "extended-release" formulation can extend the period over which drug is released or targeted to the desired site. A "delayed-release" formulation can be designed to delay the release of the pharmaceutically active compound for a specified period. Such formulations are referred to herein as "delayed-release" or "delayed-onset" formulations or dosage forms. Modified-release formulations of the present invention include those that exhibit both a delayed- and extended-release, for example, formulations that only begin releasing after a fixed period of time or after a physicochemical change has occurred, for example, then continue releasing over an extended period.

As used herein, the term "immediate-release formulation," is meant to describe those formulations in which more than about 50% of active ingredient is released from the dosage form in less than about 2 hours. Such formulations are also referred to herein as "conventional formulations."

As used herein, the phrase "drug-release profile that is independent of surrounding pH" means effectively a drug composition comprising a polymeric system that is non-enteric or whose permeability and solubility properties do not change with environmental, i.e., external, pH. Meaning, a drug composition having release characteristics such as dissolution is substantially unaffected by pH or regardless of pH-changes in the environment. This is in comparison to a release profile that is pH-dependent where the release characteristics vary according to the pH of the environment.

It is known that certain medium and long-chain fatty acids exert an intestinal epithelial effect which leads to an increased permeability of intestinal membranes to entities that may otherwise be impermeable or exhibit limited permeability. The medium chain triglycerides, including but not limited to sodium caprate, enhance absorption to a greater extent in the small intestine than in the ileum or colon (results attached). In a study to investigate the effects of the long-chain polyunsaturated fatty acids, mainly eicosapentaenoic acid (EPA) and docosahexaenoic acid (DHA) on insulin absorption from rat intestinal loops in situ, Suzuki et al demonstrated that both EPA and DHA strongly enhanced insulin absorption and induced hypoglycaemia after rectal and colonic dosing. DHA did not induce gross morphological changes in the structure of the intestinal mucosa (Suzuki et al, Journal of Pharmaceutical Sciences, Vol 87, 10: Pgs. 1196-1202); 1998). Thus, it is apparent that medium chain triglycerides enhance intestinal permeability while DHA is a possible means of facilitating the intestinal absorption of insulin and possibly other macromolecules, peptides and proteins included, without inducing any serious damage to epithelial cells. Combining poorly permeable entities with medium- or long-chain fatty acids and targeted delivery to local regions of the intestine or colon has the potential to enhance absorption of otherwise poorly permeable entities. The current invention seeks to enable such delivery through the encapsulation of entities formulated with polyunsaturated fatty acids using a gelling agent, including, but not limited to one or a mixture of gelatine, pectin, alginate or chitosan, with or without an additional colon-specific coating.

Thus, while the primary advantage of the current invention relates to enhanced colon delivery for absorption from the colon or treatment of diseased intestinal and colonic tissue, the invention also permits the development of sustained absorption of hydrophobic and lipophilic drugs that otherwise would not be soluble in the colon. By extension, the invention also facilitates the development of novel combination therapies as well as inventive chronotherapies comprising one or a multiple of drugs released at different time points.

Intestinal Diseases

Gastrointestinal conditions pose a significant worldwide health problem. Inflammatory bowel diseases, which genus encompass a range of diseases including Crohn's disease and ulcerative colitis, affect nearly 1 million people in the United States each year. The two most common inflammatory conditions of the intestine, ulcerative colitis (UC) and Crohn's disease (CD), are collectively known as inflammatory bowel disease (IBD). These conditions are diseases of the distal gut (lower small intestine, large intestine, and rectum) rather than the proximal gut (stomach and upper small intestine). Between the two, ulcerative colitis primarily affects the colon, whereas Crohn's disease affects the distal small intestine as well.

Targeted Release/Enhanced Sustained Absorption/Reduced Side Effects

Tacrolimus is differentially absorbed from in different regions of the gastrointestinal tract, being optimally absorbed from the small intestine, with ileum and colonic absorption efficiency dropping to half that observed for the small intestine. Also, a food effect is observed. After absorption from the gastrointestinal tract, drug effects persist for 8-12 hours after oral administration of conventional IR tablets. The total dosage is typically in the range of 2.5-10 mg per day, in exceptional cases rising to 20 mg/day. Under conventional dosage regimes, tacrolimus is given twice daily, typically with one dose given before breakfast and a second dose given in the late afternoon. Adverse effects, due to the initial rapid absorption from the small intestine results in above therapeutic plasma concentrations, associated with tacrolimus treatment include nephrotoxicity and the development of patient infection due to immunosuppression. There is a need for a controlled release format that prevents toxic side effects while enhancing absorption from the ileum and colon. Formulating tacrolimus in a minicapsule format, the core of which is pre-solubilised, has the potential to enhance the absorption of tacrolimus from the colon. Also, through development of a sustained release format, either through modifying the core formulation to enable sustained release or coating the surface with a sustained release polymer will reduce the peak plasma drug concentration, thereby reducing the potential dose-related side effects, including nephrotoxicity, neurotoxicity and excessive immunosuppression.

Inflammatory Bowel Disease (IBD)

Although they are distinct IBD conditions, the same drugs are commonly used to treat both UC and CD. Drugs commonly used in their treatment include steroids (e.g., budesonide and other corticosteroids, and adrenal steroids such as prednisone and hydrocortisone); cytokines such as interleukin-10; antibiotics; immunomodulating agents such as azathioprine, 6-mercaptopurine, methotrexate, cyclosporine, and anti-tumor necrosis factor (TNF) agents such as soluble TNF receptor and antibodies raised to TNF; and also antinflammatory agents such as zinc. The most commonly prescribed agents for IBD include sulfasalazine (salicyl-azosulfapyridine, or "SASP") and related 5-aminosalicylic acid ("5-ASA") products, including mesalazine.

Inflammation of the ileum (the farthest segment of the small intestine) due to Crohn's disease is known as iletis. When both the small intestine and the large intestine are involved, the condition is called Crohn's enterocolitis (or ileocolitis). Other descriptive terms may be used as well. Diagnosis is commonly made by x-ray or colonoscopy. Treatment includes medications that are anti-inflammatories, immune suppressors, or antibiotics. Surgery can be necessary in severe cases. Crohn's disease is an area of active research around the world and new treatment approaches are being investigated which have promise to improve the lives of affected patients.

Gastrointestinal Graft-Versus-Host-Disease (GI-GVHD)

GI GVHD is a life-threatening condition and one of the most common causes for bone marrow and stem cell transplant failure. These procedures are being increasingly used to treat patients with leukemia and other cancers to eliminate residual disease and reduce the likelihood of relapse. Unlike solid organ transplants where the patient's body may reject the organ, in GVHD it is the donor cells that begin to attack the patient's body—most frequently the gut, liver and skin. Patients with mild-to-moderate GI GVHD typically develop symptoms of anorexia, nausea, vomiting and diarrhea. If left untreated, GI GVHD can progress to ulcerations in the lining of the GI tract, and in its most severe form, can be fatal. Systemic immunosuppressive agents such as prednisone, which are the current standard treatments for GI GVHD, are associated with high mortality rates due to infection and debility. Further, these drugs have not been approved for treating GI GVHD in the U.S. or European Union, but rather are used off-label as investigational therapies for this indication.

The current invention, permitting colon-targeted release of tacrolimus to the colon, is a novel oral, locally acting active therapy which will reduce the need for systemic immunosuppressive drugs such as prednisone, which is currently used to prevent and control GI GVHD. Drugs such as prednisone have the unwanted and potentially dangerous side effects of weakening the patient's immune system leaving them susceptible to opportunistic infections as well as substantially inhibiting the intended anti-cancer effect of bone marrow and stem cell transplants. The colon-targeted tacrolimus therapy is designed to reduce the need for systemic immunosuppressive drugs and thereby improve the outcome of bone marrow and stem cell transplantation.

Tacrolimus, is recognized, on- and off-label, as common treatments for IBD and is widely used for this purpose. However, tactolimus therapy may continue to exhibit problems, including side effects to be detailed hereinafter. Additionally, both exhibit a half-life and efficacy profile that is less than maximal, reflected in high and multiple daily doses, lower response and remission rates, and higher relapse rates, related to its site and mechanism of action and efficiency of delivery to the cells of the distal gut. Extensive tacrolimus absorption from the small intestine reduces its availability at distal sites in the gut, which are the sites of the therapeutic effect and the preferred sites of delivery, thereby necessitating high doses to be administered. Ideally, the compound should reach the distal gut (ileum and/or colon) in unchanged form, but not be absorbed into the systemic circulation as the parent compound from there. The absorption into the systemic circulation from proximal and/or distal sites as the parent compound results in side effects associated with the absorbed drug and its systemic effects. Existing oral dosage forms of tacrolimus, namely soft or hard gelatine capsules, are unsuited to controlled or ileum/colon targeted release.

To overcome systemic side effects and the need to administer high doses frequently, the current invention proposes first formulating tacrolimus as solubilised formulations, encapsulating with a gelling agent to produce minicapsules. The encapsulating agent may contain controlled release polymers that release only in the ileum or colon or may be coated with a polymer or other coating that results in same. The advantages are several-fold, including: reduced systemic absorption of the active tacrolimus which is known to result in dose related toxicities, including nephrotoxicity, release of sufficient dose of tacrolimus in soluble form as well as a broad distribution of tacrolimus throughout the colon. Furthermore, incorporating a mucoadhesive into the encapsulating shell or coating the encapsulating shell with a mucoadhesive may ensure that the minicapsules are in contact with the colonic mucus layer prior to releasing the active proximal to the diseased tissue. For certain Crohn's Disease sub-groups it may be required to enable release throughout the gastrointestinal tract, including the small intestine. Likewise for GI-GVHD, it may be beneficial to have sustained release throughout the entire gastrointestinal tract from small intestine to colon.

The present invention provides a multiple minicapsule modified release composition comprising at least one population of tacrolimus-containing minicapsules which, upon administration to a patient, exhibits a single, bimodal or multimodal release profile throughout the entire gastrointestinal tract or at pre-specified regions along the gastrointestinal tract.

The multiple minicapsule or minisphere modified release composition may comprise at least two populations of tacrolimus-containing minicapsules which, upon administration to a patient, exhibits a bimodal or multimodal release profile that results in a plasma profile within therapeutically effective pharmacokinetic parameters.

In one case the invention provides a multiple minicapsule modified release composition comprising at least two populations of tacrolimus-containing minicapsules which, upon administration to a patient, exhibits a pulsatile release profile.

In another case the invention provides a multiple minicapsule modified release composition comprising at least two populations of tacrolimus minicapsules which, upon administration to a patient, results in a pulsatile plasma profile.

The invention also provides a multiple minicapsule modified release composition comprising at least two populations of active ingredient-containing minicapsules which, upon administration to a patient, produces a plasma profile substantially similar to the plasma profile produced by the administration of at least dosage forms, one immediate release and the other sustained release given sequentially.

In one case the invention provides a multiple minicapsule modified release composition whereby the tacrolimus is released in the ileum or colon, where the active is not absorbed but may yet be locally active.

In the invention the minicapsule core composition may include excipients in a liquid form that permit controlled or sustained release in conjunction with or independent of the shell or coating. Such forms can include various temperature modulated lipid-based, wax-like excipients, including, but not limited to the Gattefosse Gelucire® range of saturated triglycerides or the Sasol range of Witepsol® saturated triglycerides which demonstrate considerable sustained release when exposed to the gastrointestinal environment.

The minicapsule core composition may include excipients in a semi-liquid or solid form that permit controlled or sustained release in conjunction with or independent of the shell or coating or where the core comprises the entire minicapsule or minisphere.

The pharmaceutically acceptable excipient may be chosen from carriers, fillers, extenders, binders, humectants, disintegrating agents, solution-retarding agents, absorption accelerators, wetting agents, absorbents, lubricants, stabilizers, coloring agents, buffering agents, dispersing agents, preservatives, organic acids, and organic bases.

The modified-release compositions of the invention may comprise an immediate-release core and a semi-permeable membrane. In some embodiments, the modified-release compositions of the invention may comprise a modified-release semi-solid core and a semi-permeable membrane.

The present invention also provides sustained release of drugs that otherwise are readily absorbed in the small intestine but exhibit limited colonic absorption is made possible through targeted release of formulations wherein the drug or other entity is pre-solubilised. An example of such drugs includes tacrolimus.

The present invention also permits development of sustained release tacrolimus in combination with an antioxidant or nuclear factor kappa B inhibitor such as, but not limited to curcuminoids, such as, but not limited to curcumin, to reduce nephrotoxicity or increase effectiveness in treating inflammatory bowel disease or to enhance efficacy in the treatment of diabetes-related kidney disorders.

The present invention also permits development of sustained release tacrolimus, sirolimus, cyclosporine or derivatives thereof in combination with mycophenolate motefil and/or other immunomodulators to enhance the management of post-transplant treatment.

The invention also includes methods of treating inflammatory bowel disease comprising administering to a subject in need thereof a pharmaceutical composition comprising a dose of tacrolimus, or pharmaceutically acceptable salts, esters and pro-drugs thereof, and at least one pharmaceutically acceptable excipient. Such formulations are preferentially developed to ensure release in the ileum and/or colon.

Still another embodiment of this invention relates to methods of treating inflammatory bowel disease comprising administering to a subject in need thereof a pharmaceutical composition comprising tacrolimus and a curcuminoid, such as, but not limited to, curcumin, with release of same targeted to the ileum or colon.

Another embodiment of the present invention relates to development of sustained release tacrolimus in combination with the delivery of natural plant, marine or other extracts, including essential oils such as Neem, aloe vera and the omega range of polyunsaturated oils, including EPA, DHA and CLA, with or without plant extracts such as, but not limited to, berry extracts, tripala, tumeric, resveratrol, resorcinolic/phenolic lipids, flavanoids and any natural or synthetic derivatives thereof.

Another embodiment of the present invention relates to a pharmaceutical composition comprising a combination of any of the above examples released anywhere along the gastrointestinal tract.

Another embodiment of the current invention relates to non-covalent complexion of a drug with a carrier such as cyclodextrins, maltodextrins, dextrins or modifications thereof and targeting the release of such to the specific sites along the gastrointestinal tract.

Yet a further embodiment of the present invention is targeted gastrointestinal release of formulations containing conjugated drugs, the conjugation which prevents absorption into the systemic or lymphatic vasculature yet retains local intestinal therapeutic efficacy.

Still a further embodiment of the present invention is targeted gastrointestinal release of formulations comprising poorly soluble actives, including small molecules and biopharmaceuticals formulated with amongst other excipients, permeability enhancers, such as, but not limited to, sodium dodecanoate (C12), Sodium Caprate (C10) and/or Sodium Palmitate (C16).

In the current invention, in the development of treatments for organ graft rejection, the active pharmaceutical ingredient is interchangeable, including any one or combination of tacrolimus with any one of EPA, DHA, natural plant extracts, natural marine extracts or other biological and active entities, which may include siRNA constructs.

In the current invention, in the development of treatments for inflammatory bowel disease, the active pharmaceutical ingredient is interchangeable, including any one or combination of tacrolimus with any one of EPA, DHA, natural plant extracts, natural marine extracts or other biological and active entities, which may include siRNA constructs.

In the current invention, in the development of treatments for Graft-Versus-Host Disease, the active pharmaceutical ingredient is interchangeable, including any one or combination of tacrolimus with any one of EPA, DHA, natural plant extracts, natural marine extracts or other biological and active entities, which may include siRNA constructs.

In the current invention, the immunological modulating entities, including antigens, adjuvants, emulsions, oils, and small molecules are interchangeable and may be utilised for the development of vaccines, oral tolerance modulators and allergen modulators, which may include siRNA constructs.

The invention allows for the development of solid-, semi-solid or liquid-filled minicapsules comprising one or more layer and produced using conventional seamless minicapsule processes, modified melt extrusion, non-pareil coating, non-pareil drug layering or other processes that enable the production of the desired dosage form.

The invention provides a solid oral dosage form comprising the multiple minicapsule modified release composition of the present invention, the said minicapsules being one layer or multiple layers. Where a two layer minicapsule has a shell comprised of a gelling agent with a controlled release polymer or other coating or comprised of controlled release polymer or other materials.

The invention also provides a sachet format comprising multiple minicapsule modified release composition of the present invention for ease of administration to paediatrics, geriatrics or other patient populations with swallowing difficulties.

The invention will be more clearly understood from the following examples.

EXAMPLES

Figure 7:
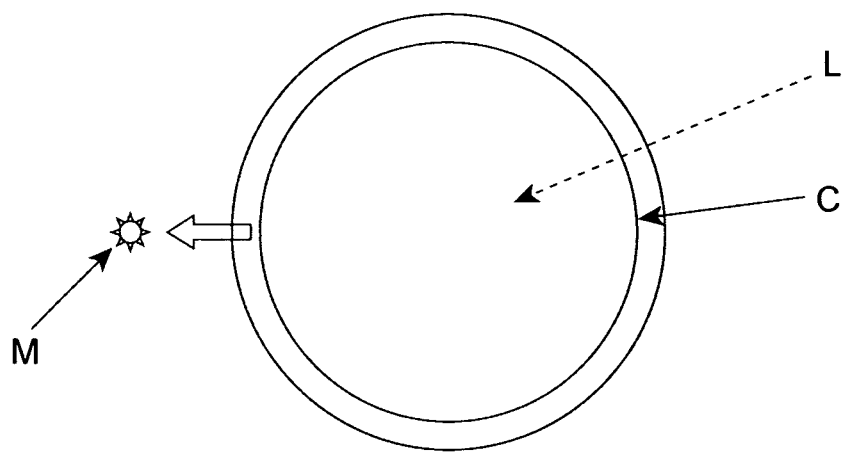
FIG. 7 is a schematic illustration of a liquid filled minicapsule of the type used in the formulations of the invention.

FIG. 7 illustrates liquid-filled minicapsule with controlled release polymer coatings. This format comprises an active substance L encapsulated using a suitable gelling agent C that may be further coated to permit controlled or targeted release along the gastrointestinal tract. The active substance is in an enhanced solubilised or permeabilised form. The open arrow represents the release of a drug molecule M into the external medium, where it is fully soluble when released;

Example 1

Once-Daily Tacrolimus

The core formulation was prepared as follows. Tacrolimus was dissolved in a suitable volume of ethanol. Once dissolved, the solution was blended with a suitable mix of Labrafil and Olive oil. The shell solution was prepared as follows: Appropriate quantities of gelatin and sorbitol were added to water and heated to 70 degrees C. until in solution. The minicapsules were prepared using a Spherex Labo to produce 2-layer minicapsules, the core of which comprises Tacrolimus in an enhanced solubilised and permeabilised formulation. In addition, the core formulation does enable a degree of sustained release.

TABLE 1

Once-daily Tacrolimus

| Ingredients | % w/w |
|---|---|
| Core Composition | |
| Tacrolimus | 3.25 |
| Labrafil | 36.4 |
| Olive Oil | 47.65 |
| Ethanol | 12.7 |
| Shell Composition | |
| Gelatin | 90.0 |
| Sorbitol | 10.0 |

Example 2

Tacrolimus release from uncoated minicapsules of Example 1: Dissolution profiles in FIG. 1 demonstrate the following release of tacolimus from minicapsules expressed as a percentage of the total minicapsule content: less than 55% within 1 hr; less than 80% within 4 hrs; less than 90% within 12 hrs and less than or equal to 100% at 24 hr.

Example 3

Figure 2:
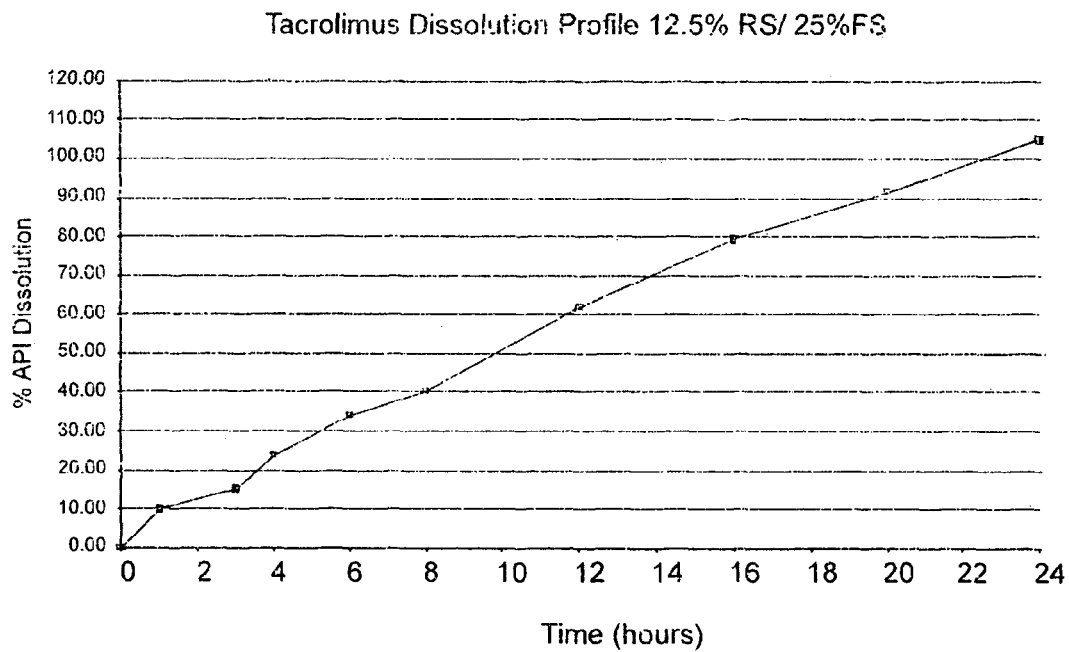
FIG. 2 is a graph showing the dissolution profile for tacrolimus minicapsules coated with 12.5% Eudragit™ RS30D followed by 25% Eudragit™ FS30D.

Tacrolimus release from minicapsules of Example 1 coated with 12.5% weight gain Eudragit™ RS30D followed by 25% weight gain Eudragit™ FS30D: Dissolution profiles in FIG. 2 demonstrate the following release of tacolimus from minicapsules expressed as a percentage of the total minicapsule content: less than 10% within 1 hr; less than 30% within 4 hrs; less than 75% within 12 hrs and less than or equal to 100% at 24 hr. This is suited either to a once-daily systemic absorption product or an ileum/colon-specific product.

Example 4

Figure 3:
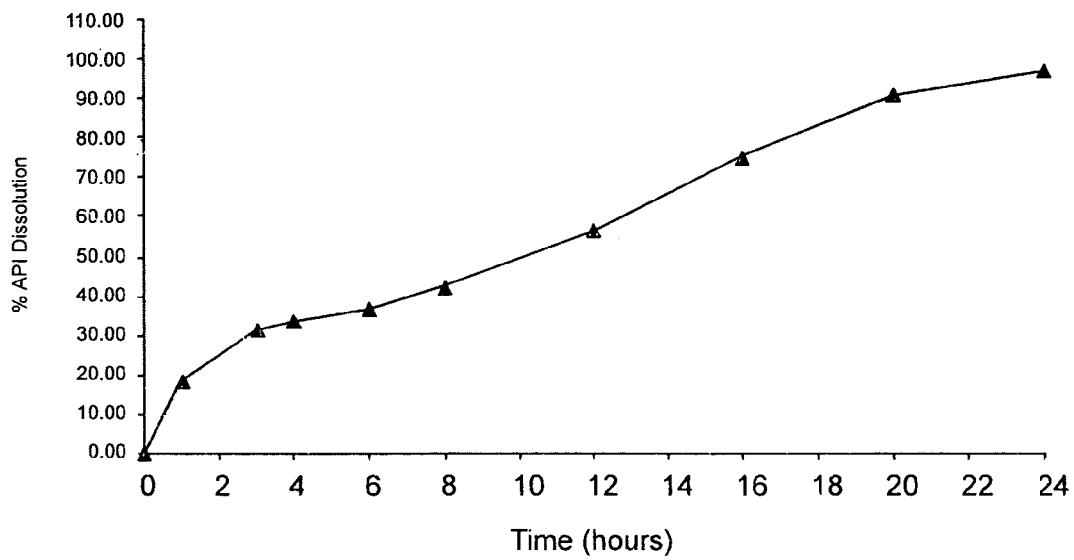
FIG. 3 is a graph showing the dissolution profile for composite tacrolimus minicapsules—30% uncoated (immediate release) and 70% coated with 12.5% Eudragit™ RS30D followed by 25% Eudragit™ FS30D.

Tacrolimus release from a composite of minicapsules of Example 1 comprising 30% (by potency) uncoated and 70% (by potency) coated with 12.5% weight gain Eudragit™ RS30D followed by 25% weight gain Eudragit™ FS30D: Dissolution profiles in FIG. 3 demonstrate the following release of tacolimus from minicapsules expressed as a percentage of the total minicapsule content: less than 20% within 1 hr; less than 35% within 4 hrs; less than 65% within 12 hrs and less than or equal to 100% at 24 hr.

Example 5

Figure 4:
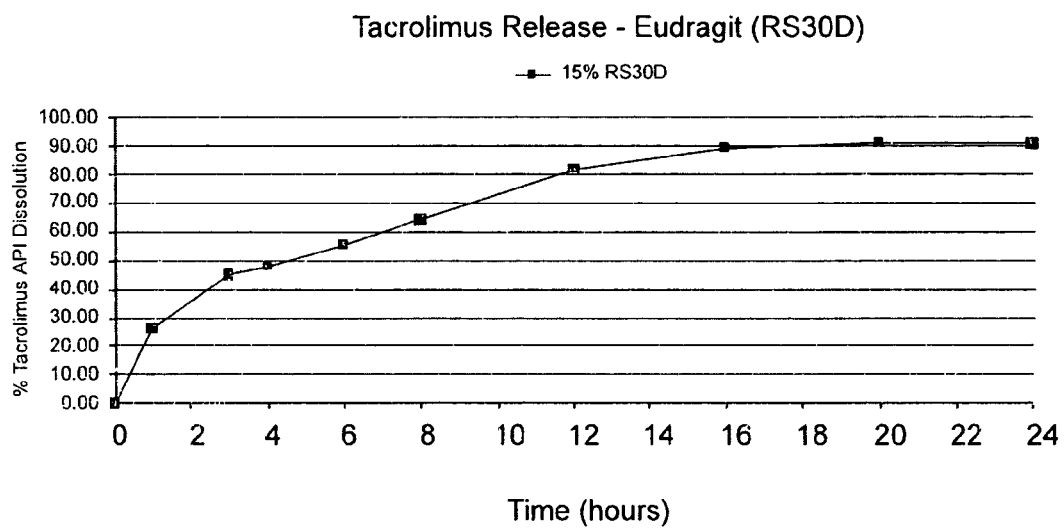
FIG. 4 is a graph showin the dissolution profile for 15% weight gain Eudragit™ profile for 15% weight gain Eudragit™ RS30D—coated tacrolimus minicapsules.

Tacrolimus release from minicapsules of Example 1 coated with 15% weight gain Eudragit™ RS30D: Dissolution profiles in FIG. 4 demonstrate the following release of tacolimus from minicapsules expressed as a percentage of the total minicapsule content: less than 30% within 1 hr; less than 50% within 4 hrs; less than 85% within 12 hrs and less than or equal to 100% at 24 hr.

Example 6

Figure 5:
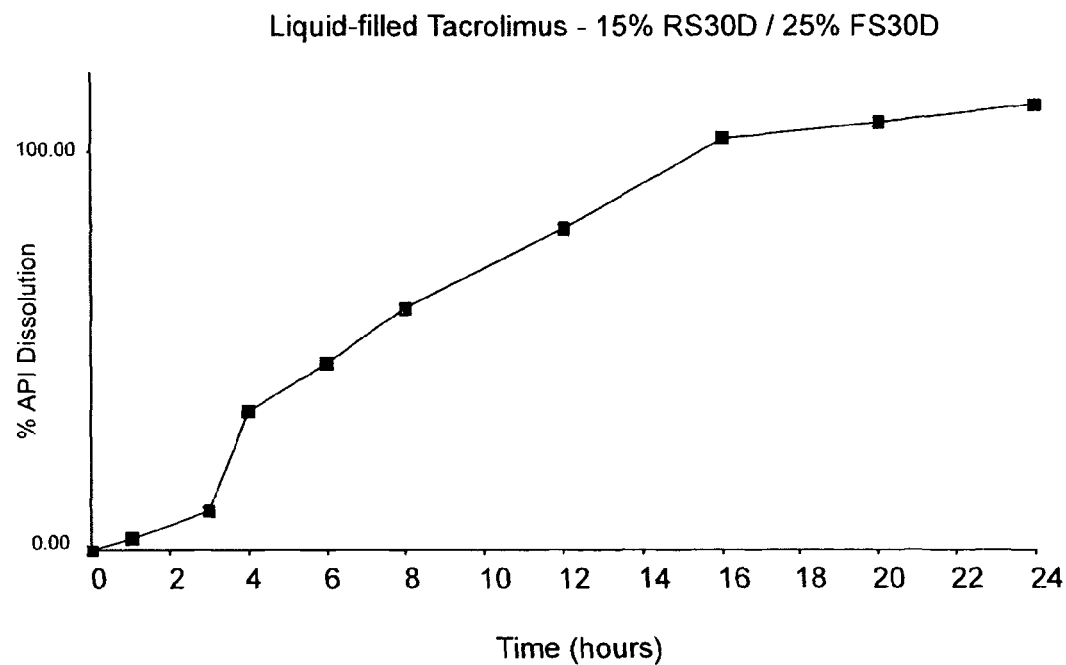
FIG. 5 is a graph showing the dissolution profile for 15% weight gain Eudragit™ RS30D/25% weight gain Surlease®—coated tacrolimus minicapsules.

Tacrolimus release from a minicapsules of Example 1 coated with 15% weight gain Eudragit™ RS30D followed by 25% weight gain Eudragit™ FS30D: Dissolution profiles in FIG. 5 demonstrate the following release of tacolimus from minicapsules expressed as a percentage of the total minicapsule content: less than 10% within 1 hr; less than 30% within 4 hrs; less than 75% within 12 hrs and less than or equal to 100% at 24 hr. This is suited either to a once-daily systemic absorption product or, more particularly, an ileum/colon-specific product.

Example 7

Figure 6:
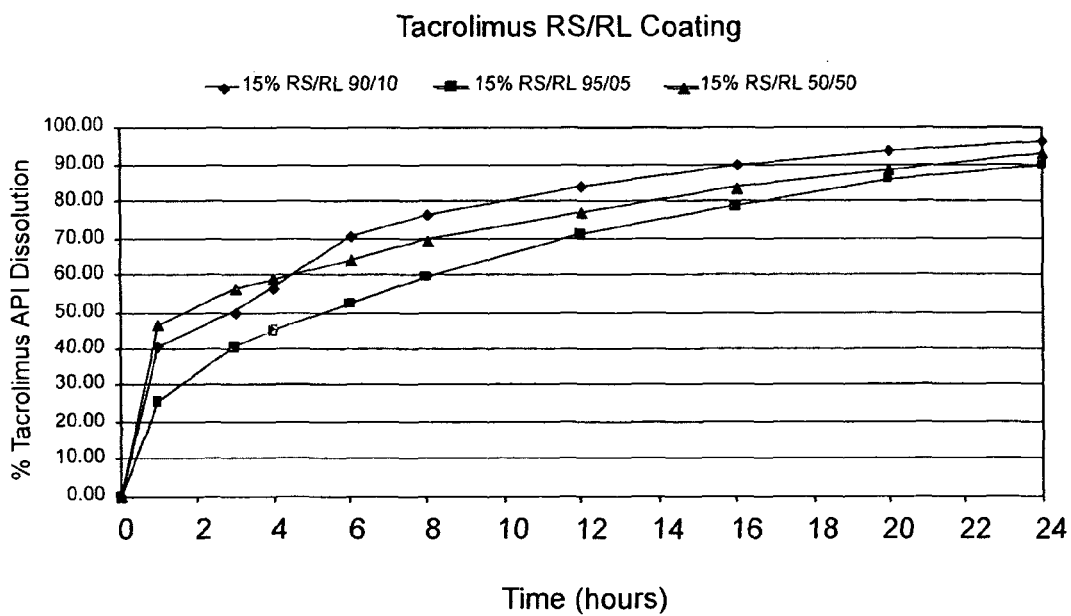
FIG. 6 is a graph showing the dissolution profile for 15% weight gain variable RS/RL coatings.

Tacrolimus release from minicapsules of Example 1 coated with a combination of Eudragit™ RS and Eudragit™ RL in the following ratios—90:10, 95:05 and 50:50: Dissolution profiles in FIG. 6 demonstrate the following release of tacolimus from minicapsules expressed as a percentage of the total minicapsule content: greater than 20% and less than 50% within 1 hr; greater than 35% and less than 60% within 4 hrs; greater than 65% and less than 90% within 12 hrs and greater than 90% at 24 hr.

Example 8

Once-Daily Tacrolimus

The core formulation was prepared as follows: Tacrolimus was added to a suitable volume Gelcuire 33/01 heated and stirred until dissolved. Once dissolved, the solution was blended with a suitable volume of Olive oil.

The shell solution was prepared as follows: Appropriate quantities of gelatin and sorbitol were added to water and heated to 70 degrees C. until in solution.

The minicapsules were prepared using a Spherex Labo to produce 2-layer minicapsules, the core of which comprises Tacrolimus in an enhanced solubilised and permeable formulation. In addition, the core formulation is inherently sustained release.

TABLE 2

Once-daily Tacrolimus

| Ingredients | % w/w |
|---|---|
| Core Composition | |
| Tacrolimus | 0-10 |
| Gelucire 33/01 | 0-75 |
| Olive Oil | 0-75 |
| Ethanol | 0-20 |
| Shell Composition | |
| Gelatin | 90.0 |
| Sorbitol | 10.0 |

The sustained release coating comprises a 95:5 ratio of Eudragit™ RS: Eudragit™ RL. The combination comprises 95:5 Eudragit™ RS:RL, further coated with Eudragit FS30D.

Example 9

Once-Daily Tacrolimus

The core formulation was prepared as follows: Tacrolimus was added to a suitable volume Gelcuire 44/01 heated and stirred until dissolved. Once dissolved, the solution was blended with a suitable volume of Fish oil.

The shell solution was prepared as follows: Appropriate quantities of gelatin and sorbitol were added to water and heated to 70 degrees C. until in solution.

The minicapsules were prepared using a Spherex Labo to produce 2-layer minicapsules, the core of which comprises Tacrolimus in an enhanced solubilised and permeable formulation. In addition, the core formulation is inherently sustained release.

TABLE 3

Once-daily Tacrolimus

| Ingredients | % w/w |
|---|---|
| *Core Composition* | |
| Tacrolimus | 0-10 |
| Gelucire 44/01 | 0-75 |
| Fish Oil | 0-75 |
| Ethanol | 0-20 |
| *Shell Composition* | |
| Gelatin | 90.0 |
| Sorbitol | 10.0 |

Tacrolimus is released from uncoated minicapsules as follows: 50% released within 4 hours; 100% within 12 hours. To enable a once-daily product, the minicapsules will be coated either with a sustained release polymer or a combination of colonic-specific polymer and sustained release polymers. The sustained release coating comprises Surelease®, with or without the inclusion of high or low molecular weight pectin in the coating solution and with or without further coating the mincapsules with the pH sensitive Eudragit™ FS30D.

Example 10

Ileum- and Colon-Specific Tacrolimus

The core formulation was prepared as follows. Tacrolimus was dissolved in a suitable volume of ethanol. Once dissolved, the solution was blended with a suitable mix of Labrafil and Olive oil. The shell solution was prepared as follows: Appropriate quantities of gelatin and sorbitol were added to water and heated to 70 degrees C. until in solution. The minicapsules were prepared using a Spherex Labo to produce 2-layer minicapsules, the core of which comprises tacrolimus in an enhanced solubilised and permeabilised formulation. In addition, the core formulation does include the addition of ileum and/or colon specific release polymer coatings to enable a degree of targeted and/or release.

TABLE 4

Ileum- and Colon-specific Tacrolimus

| Ingredients | % w/w |
|---|---|
| *Core Composition* | |
| Tacrolimus | 3.25 |
| Labrafil | 36.4 |
| Olive Oil | 47.65 |
| Ethanol | 12.7 |
| *Shell Composition* | |
| Gelatin | 90.0 |
| Sorbitol | 10.0 |

To enable an ileum- and colon-specific product, the minicapsules are coated either with a sustained release polymer or a combination of colonic-specific polymer and sustained release polymers. The sustained release coating comprises minicapsules coated with 12.5% weight gain Eudragit™ RS30D followed by 25% weight gain Eudragit™ FS30D.

Example 11

Ileum- and Colon-Specific Tacrolimus

The core formulation was prepared as follows. Tacrolimus was dissolved in a suitable volume of ethanol. Once dissolved, the solution was blended with a suitable mix of Labrafil and Neem oil. The shell solution was prepared as follows: Appropriate quantities of gelatin and sorbitol were added to water and heated to 70 degrees C. until in solution. The minicapsules were prepared using a Spherex Labo to produce 2-layer minicapsules, the core of which comprises tacrolimus in an enhanced solubilised and permeabilised formulation. In addition, the core formulation does enable a degree of sustained release.

TABLE 5

Ileum- and Colon-specific Tacrolimus

| Ingredients | % w/w |
|---|---|
| *Core Composition* | |
| Tacrolimus | 2.5-25 |
| Labrafil | 15-35 |
| Neem | 32.5-70 |
| Ethanol | 12.5 |
| *Shell Composition* | |
| Gelatin | 90.0 |
| Sorbitol | 10.0 |

To enable an ileum- and colon-specific product, the minicapsules can be coated either with a sustained release polymer or a combination of colonic-specific polymer and sustained release polymers.

Example 12

Ileum- and Colon-Specific Tacrolimus

The core formulation was prepared as follows. Tacrolimus was dissolved in a suitable volume of ethanol. Once dissolved, the solution was blended with a suitable mix of Labrafil and Fish oil. The shell solution was prepared as follows: Appropriate quantities of gelatin and sorbitol were added to water and heated to 70 degrees C. until in solution. The minicapsules were prepared using a Spherex Labo to produce 2-layer minicapsules, the core of which comprises tacrolimus in an enhanced solubilised and permeabilised formulation. In addition, the core formulation does enable a degree of sustained release.

TABLE 6

Ileum- and Colon-specific Tacrolimus

| Ingredients | % w/w |
|---|---|
| *Core Composition* | |
| Tacrolimus | 2.5-25 |
| Labrafil | 15-35 |
| Fish Oil | 32.5-70 |
| Ethanol | 12.5 |
| *Shell Composition* | |
| Gelatin | 90.0 |
| Sorbitol | 10.0 |

To enable an ileum- and colon-specific product, the minicapsules can be coated either with a sustained release polymer as a combination of Surelease® and USP Pectin in a 2:1 w/w ratio with a 30% weight gain.

Example 13

Ileum- and Colon-Specific Tacrolimus

The core formulation was prepared as follows. Polyethylene glycol 400, Glyceryl Monooleate and Decaglyceryl monooleate were mixed together at 50 degrees C. until in solution. Tacrolimus together with the propylene glycol and tocopherol linoleate where added and the mixture stirred under an inert gas blanket until dissolved. The shell solution was prepared as follows: Appropriate quantities of gelatin and sorbitol were added to water and heated to 70 degrees C. until in solution. The minicapsules were prepared using a Spherex Labo to produce 2-layer minicapsules, the core of which comprises tacrolimus in an enhanced solubilised and permeabilised formulation. In addition, the core formulation does enable a degree of sustained release.

TABLE 7

Ileum- and Colon-specific Tacrolimus

| Ingredients | % w/w |
|---|---|
| Core Composition | |
| Tacrolimus | 2.5-25 |
| Polyethylene glycol 400 | 5-50 |
| Glyceryl Monooleate | 5-50 |
| Decaglyceryl monooleate | 10-60 |
| Propylene glycol | 2.5-25 |
| Tocopherol linoleate | 0-1.5 |
| Shell Composition | |
| Gelatin | 90.0 |
| Sorbitol | 10.0 |

To enable an ileum- and colon-specific product, the minicapsules can be coated either with a sustained release polymer as a combination of Surelease® and USP Pectin in a 2:1 w/w ratio with a 30% weight gain.

Example 13

Coatings

The following options have been developed and tested:

Eudragit™ RS—Tacrolimus containing minicapsules were coated with Eudragit™ RS with or without further coating with Eudragit™ FS30D.

Surelease®—Tacrolimus containing minicapsules were coated with Surelease® with or without further coating with Eudragit™ FS30D.

Surelease® and Pectin—Tacrolimus containing minicapsules were coated with Surelease®, with or without the inclusion of high or low molecular weight pectin in the coating solution and with or without further coating the mincapsules with the pH sensitive Eudragit™ FS30D.

Surelease® and Alginate—Tacrolimus containing minicapsules were coated with Surelease®, with or without the inclusion of alginate in the coating solution and with or without further coating the mincapsules with the pH sensitive Eudragit™ FS30D.

The sustained release coating may comprise a combination of Surelease® and USP Pectin in a 2:1 w/w ratio with a 30% weight gain. Alternatively, the sustained release coating may comprise Eudragit™ RS with a weight gain of 22%.

The once-daily formulation will typically comprise a blend of uncoated and coated minicapsules to provide 0-50% release between 6 and 12 hours and 0-100% release between 12 and 24 hours.

The invention envisages the use of a tacrolimus formulation in combination with another therapeutically or propylactically active entity or entities, as single fixed combination dosage form or to be administered separately.

For the treatment or prevention of solid-organ transplant rejection, other immunosuppressants could be considered, either alone or in combination with tacrolimus or derivatives thereof. These include, but are not limited to, various other calcineurin inhibitors such as but not limited to Abetimus, Deforolimus, Everolimus, Gusperimus, Pimecrolimus, Sirolimus, Cyclosporins, Temsirolimus; glucocorticosteriods such as but not limited to Cortisone, Hydrocortisone, Fludrocortisone, Prednisone, Prenisolone, Methylpredilisolone, Triamcinolone, Betamethasone, Dexamethasone or Paramethasone; cytostatics such as but not limited to Anakinra, Azathioprine, Leflunomide, Methotrexate, Mycophenolic acid, Thalidomide; antibodies such as the T-cell receptor directed anti-CD3 OKT3; the immunophilin receptor binder sirolimus; interferons; opioids; TNFα-binding proteins, including, but not limited to, infliximab, etanercept, adalimumab, cucumin and catechins; and Mycophenolate Mofetil acid which acts as a non-competitive, selective and reversible inhibitor of inosine monophosphate dehydrogenase. The above list include derivatives thereof, including those modified to include a conjugated. NO donor.

The invention is not limited to the embodiments hereinbefore described which may be varied in detail.

The invention claimed is:

1. An oral tacrolimus composition comprising seamless minicapsules having a core composition that comprises a hydrophobic liquid comprising tacrolimus in a solubilised liquid form, the minicapsules having a release profile to release the solubilised tacrolimus throughout the entire gastrointestinal tract, the minicapsules comprising a gelled state of a suspension that is a mixture of a solution comprising a gelling agent and of the hydrophobic liquid comprising tacrolimus, the gelling agent encapsulating the hydrophobic liquid comprising tacrolimus.

2. The composition of claim 1 wherein the hydrophobic liquid comprises tacrolimus, a solubilisation agent, a co-emulsifier, a surfactant, a permeability enhancer and a carrier.

3. The composition of claim 2, wherein the solubilisation agent comprises ethanol or a triglyceride; the co-emulsifying agent comprises fatty acid ester complexes; the surfactant comprises fatty acid ester complexes; and the carrier comprises a hydrophobic liquid.

4. The composition of claim 1 wherein the minicapsules are administered in a hard gelatine capsule, a sprinkle, or a tablet.

5. The composition of claim 1 wherein the minicapsules have a release profile to release pre-solubilised tacrolimus in one or more of the small intestine, the ileum or the colon.

6. The composition of claim 1 wherein the minicapsules are seamless minicapsules obtainable by formulating tacrolimus as a solubilised formulation and encapsulating the solubilised formulation with a gelling agent, wherein the solubilised formulation comprises tacrolimus in combination with a pharmaceutically acceptable carrier that comprises a hydrophobic liquid and wherein the solubilised formulation is encapsulated by ejecting it through a nozzle having a single orifice in a mixed suspension which further comprises a solution comprising the gelling agent as well as the solubilised tacrolimus formulation, the ejected suspension forming into a spherical form and falling into a cooling air flow or a cooling or hardening solution where the gelling agent becomes gelled.

7. The composition of claim 6 wherein the gelling agent is gelatin.

8. The composition of claim 1 wherein the gelling agent is gelatin.

9. Minicapsules, wherein the minicapsules have a core composition that comprises tacrolimus and the minicapsules are seamless minicapsules obtainable by formulating tacrolimus as a solubilised formulation and encapsulating the solubilised formulation with a gelling agent, wherein the solubilised formulation comprises tacrolimus in combination with a pharmaceutically acceptable carrier that comprises a hydrophobic liquid and wherein the solubilised formulation is encapsulated by ejecting it through a nozzle having a single orifice in a mixed suspension which further comprises a solution comprising the gelling agent as well as the solubilised tacrolimus formulation, the ejected suspension forming into a spherical form and falling into a cooling air flow or a cooling or hardening solution where the gelling agent becomes gelled.

10. Tacrolimus for use in treating or reducing the risk of solid organ transplant rejection, graft-versus-host disease, gastro-intestinal graft-versus-host disease, inflammatory bowel disease, ulcerative colitis, or Crohn's disease, wherein he tacrolimus is comprised in an oral formulation which permits targeted release of the tacrolimus to specific regions of the gastrointestinal tract, the oral formulation comprising minicapsules of claim 9.

11. The minicapsules of claim 9, the minicapsules being in a composition comprising a first population of said minicapsules and a second population of said minicapsules.

12. An oral tacrolimus composition comprising minicapsules as claimed in claim 9 wherein the minicapsules have a release profile to release solubilised tacrolimus in one or more of the small intestine, the ileum or the colon.

13. A composition as claimed in claim 12 wherein the tacrolimus is present in the core in an amount of from 2.5 to 15% w/w.

14. The composition as claimed in claim 12 wherein the minicapsules are modified to provide the release profile, wherein a modified release is attributable to a polymer coating.

15. The composition as claimed in claim 14 wherein the coating includes a dissolution enhancing agent, wherein the dissolution enhancing agent is degraded by bacteria normally present in the gastrointestinal tract.

16. The composition of claim 12 wherein the composition comprises a first population of minicapsules comprising tacrolimus and a second population of minicapsules comprising tacrolimus.

17. The composition of claim 16 wherein the first population comprises uncoated minicapsules and wherein the second population comprises coated minicapsules.

18. The composition of claim 16, which comprises from 10 to 40% w/w uncoated minicapsules and from 60 to 90% w/w coated minicapsules.

19. The composition of claim 12 which further comprises excipients to enhance permeability of the ileum and/or colon to tacrolimus.

20. The composition of claim 12, which further comprises excipients to enhance the therapeutic potential of tacrolimus in the ileum and colon, wherein the excipients are selected from one or more of absorption limiters, absorption enhancers, surfactants, co-surfactants, co-solvents, essential oils, natural plant extracts, ion-exchange resins, bacteria degradable conjugation linkers, polysaccharides, guar gum, pectin, chitosan, inulin and cyclodextrins.

21. The composition of claim 20 which further comprises excipients to enhance systemic bioavailability of tacrolimus following absorption throughout the gastrointestinal tract, wherein the excipients comprise efflux pump inhibitors.

22. A method for the treatment or reduction of the risk of solid organ transplant rejection; graft- versus-host disease, gastro-intestinal graft-versus-host disease, inflammatory bowel disease, ulcerative colitis, Crohn's disease, intestinal inflammations/allergies, neurodegenerative diseases, rheumatoid arthritis, systemic lupus erythematosis, hyperimmunoglobulin E, Hashimoto's thyroiditis, multiple sclerosis, progressive systemic sclerosis, myasthenia gravis, type 1 diabetes, uveitis, allergic encephalomyelitis, glomerulonephritis, and infectious diseases caused by pathogenic microorganisms, the method comprising administering to a subject a therapeutically effective amount of tacrolimus comprised in the composition of claim 12.

23. A composition of claim 12 that is combined with at least one other active pharmaceutical ingredient in a single oral dosage form, or is combined with SiRNA constructs, mycophenolate mofetil, or a natural plant or marine extract, wherein the other active pharmaceutical ingredient is selected from abetimus, deforolimus, everolimus, gusperimus, pimecrolimus, sirolimus, cyclosporins, temsirolimus, cortisone, hydrocortisone, fludrocortisone, prednisone, prenisolone, methylpredilisolone, triamcinolone, betamethasone, dexamethasone, paramethasone. anakinra, azathioprine, leflunomide, methotrexate, mycophenolic acid, thalidomide, antibodies, sirolimus, interferons, opioids, infliximab, etanercept, adalimumab, cucumin, catechins, mycophenolate mofetil acid, and any of the aforesaid when conjugated to an NO donor.

24. An oral tacrolimus composition comprising minicapsules having a core composition that comprises a hydrophobic liquid comprising tacrolimus in a solubilised liquid form, the minicapsules being seamless minicapsules and having a release profile to release the solubilised in the small intestine, the ileum and/or the colon, the minicapsules comprising a gelled state of a suspension that is a mixture of a solution comprising a gelling agent and of the hydrophobic liquid comprising tacrolimus, the gelling agent encapsulating the hydrophobic liquid comprising tacrolimus.

25. The composition of claim 24 wherein the minicapsules have a release profile to release solubilised tacrolimus in the small intestine, the ileum and the colon.

26. The composition of claim 24 wherein the gelling agent is selected from gelatin, pectin and chitosan, and combinations thereof.

27. The composition of claim 24 wherein the minicapsules are seamless minicapsules obtainable by formulating tacrolimus as a solubilised formulation and encapsulating the solubilised formulation with a gelling agent, wherein the solubilised formulation comprises tacrolimus in combination with a pharmaceutically acceptable carrier that comprises a hydrophobic liquid and wherein the solubilised formulation is encapsulated by ejecting it through a nozzle having a single orifice in a mixed suspension which further comprises a solution comprising the gelling agent as well as the solubilised tacrolimus formulation, the ejected suspension forming into a spherical form and falling into a cooling air flow or a cooling or hardening solution where the gelling agent becomes gelled.

28. The composition of claim 27 wherein the gelling agent is gelatin.

* * * * *